US011409097B2

(12) United States Patent
    Okita

(10) Patent No.: US 11,409,097 B2
(45) Date of Patent: Aug. 9, 2022

(54) VARIABLE STIFFNESS DEVICE, ENDOSCOPE, AND STIFFNESS VARYING METHOD

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 301 days.

(21) Appl. No.: 16/864,243

(22) Filed: May 1, 2020

(65) Prior Publication Data
    US 2020/0257105 A1    Aug. 13, 2020

Related U.S. Application Data

(63) Continuation of application No. PCT/JP2017/039747, filed on Nov. 2, 2017.

(51) Int. Cl.
    *A61B 1/005*    (2006.01)
    *G02B 23/24*    (2006.01)

(52) U.S. Cl.
    CPC ........ *G02B 23/2476* (2013.01); *A61B 1/0055* (2013.01)

(58) Field of Classification Search
    None
    See application file for complete search history.

(56) References Cited

U.S. PATENT DOCUMENTS

| 8,444,547 | B2 * | 5/2013 | Miyamoto | A61B 1/018 |
| | | | | 600/106 |
| 9,456,736 | B2 * | 10/2016 | Onuki | A61B 1/0125 |
| 9,763,561 | B2 * | 9/2017 | Moriyama | A61B 1/00154 |
| 9,980,632 | B2 * | 5/2018 | Banju | A61B 1/0051 |

(Continued)

FOREIGN PATENT DOCUMENTS

| JP | H05-091971 A | 4/1993 |
| JP | H09-253032 A | 9/1997 |
| JP | 2002-177199 A | 6/2002 |

(Continued)

OTHER PUBLICATIONS

NPL search at Google Patents; 2022. (Year: 2022).*

(Continued)

*Primary Examiner* — Luis Perez-Fuentes
(74) *Attorney, Agent, or Firm* — Scully, Scott, Murphy & Presser, P.C.

(57) ABSTRACT

A variable stiffness device includes a first elongated member, and a second elongated member movable along the first member. The first member includes first high bending stiffness sections, first low bending stiffness sections, and a reinforcement member reinforcing a strength of the first member. The reinforcement member includes a contact coil formed of a first wire spirally wound around a longitudinal axis of the reinforcement member, and a stranded tube formed of second wires that are twisted around each other. The second member includes a second high bending stiffness section, and a second low bending stiffness section. The second member is configured to move inside the reinforcement member, thereby changing a stiffness of the variable stiffness device.

14 Claims, 13 Drawing Sheets

(56) References Cited

U.S. PATENT DOCUMENTS 10,231,605 B2 * 3/2019 Akui .................... A61B 1/0052
11,298,008 B2 * 4/2022 Nakaji ............... A61B 1/00128

FOREIGN PATENT DOCUMENTS

JP    2004-190167 A    7/2004
JP    2007-054125 A    3/2007

OTHER PUBLICATIONS

International Search Report dated Jan. 9, 2018 issued in International Application No. PCT/JP2017/039747.
English translation of International Preliminary Report on Patentability dated May 14, 2020, together with the Written Opinion received in related International Application No. PCT/JP2017/039747.

* cited by examiner

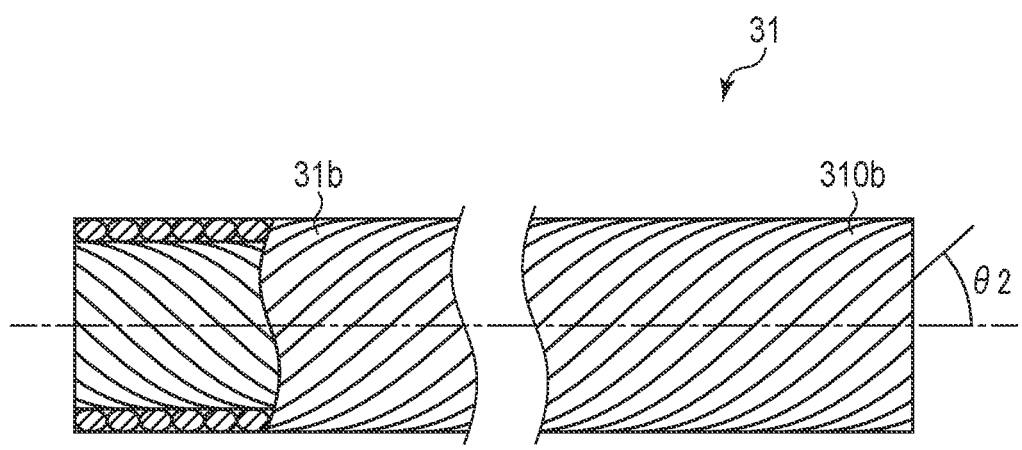
F I G. 16

US 11,409,097 B2

VARIABLE STIFFNESS DEVICE, ENDOSCOPE, AND STIFFNESS VARYING METHOD

CROSS-REFERENCE TO RELATED APPLICATIONS

This application is a Continuation Application of PCT Application No. PCT/JP2017/039747, filed Nov. 2, 2017, the entire contents of which are incorporated herein by reference.

BACKGROUND OF THE INVENTION

1. Field of the Invention

The present invention relates to a variable stiffness device configured to provide a flexible member with different levels of stiffness, an endoscope including the variable stiffness device, and a stiffness varying method of the variable stiffness device.

2. Description of the Related Art

Jpn. Pat. Appln. KOKAI Publication No. H5-91971 discloses an endoscope capable of varying the stiffness of a flexible portion of an insertion section. In this endoscope, both ends of a variable member (e.g., a coil pipe) having variable flexibility are fixed to predetermined positions of the endoscope, and an adjustment member for adjusting the flexibility of the variable member (e.g., a flexibility adjustment wire inserted into the coil pipe) is fixed to the variable member. The variable member and the adjustment member extend to a control section of the endoscope along the flexible portion, and extend over substantially the entire flexible portion. By pulling the adjustment member, the variable member is compressed and hardened, thereby changing the stiffness of the flexible portion.

BRIEF SUMMARY OF THE INVENTION

A variable stiffness device according to the present invention comprises a first elongated member, and a second elongated member movable along the first elongated member. The first elongated member includes first high bending stiffness sections, first low bending stiffness sections having a bending stiffness lower than a bending stiffness of the first high bending stiffness sections, and a reinforcement member reinforcing a strength of the first elongated member, the reinforcement member being of a metal material and having a hollow shape. The reinforcement member includes a contact coil formed of a first wire, the first wire being arranged substantially perpendicular to a longitudinal axis direction of the reinforcement member and spirally wound around a longitudinal axis of the reinforcement member, and a stranded tube formed of second wires, the second wires being arranged substantially in parallel to the longitudinal axis direction of the reinforcement member and twisted around each other. The second elongated member includes at least one second high bending stiffness section, and at least one second low bending stiffness section having a bending stiffness lower than a bending stiffness of the second high bending stiffness section. The second elongated member is configured to move inside the reinforcement member along the longitudinal axis direction of the reinforcement member, so as to change a position of the second elongated member with respect to the first elongated member, thereby varying a stiffness of a part of the variable stiffness device.

An endoscope according to the present invention comprises a flexible member and the abovementioned variable stiffness device. The variable stiffness device is installed in the flexible member and configured to provide the flexible member with different levels of stiffness.

An aspect of the present invention is directed to a stiffness varying method of a variable stiffness device. The variable stiffness device comprises a first elongated member, and a second elongated member movable along the first elongated member. The first elongated member includes first high bending stiffness sections, first low bending stiffness sections having a bending stiffness lower than a bending stiffness of the first high bending stiffness sections, and a reinforcement member reinforcing a strength of the first elongated member, the reinforcement member being of a metal material and having a hollow shape. The reinforcement member includes a contact coil formed of a first wire, the first wire being arranged substantially perpendicular to a longitudinal axis direction of the reinforcement member and spirally wound around a longitudinal axis of the reinforcement member, and a stranded tube formed of second wires, the second wires being arranged substantially in parallel to the longitudinal axis direction of the reinforcement member and twisted around each other. The second elongated member includes at least one second high bending stiffness section, and at least one second low bending stiffness section having a bending stiffness lower than a bending stiffness of the second high bending stiffness section. The stiffness varying method comprises moving the second elongated member inside the reinforcement member along the longitudinal axis direction of the reinforcement member, so as to change a position of the second elongated member with respect to the first elongated member, thereby varying a stiffness of a part of the variable stiffness device.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 16 is a diagram showing an example of a metal reinforcement member shown in FIG. 15.

DETAILED DESCRIPTION OF THE INVENTION

Hereinafter, each embodiment of the present invention will be described with reference to the drawings. In some drawings, some of the members are not shown so as to clarify the illustration.

First Embodiment

Hereinafter, a first embodiment of the present invention will be described.

Figure 1:
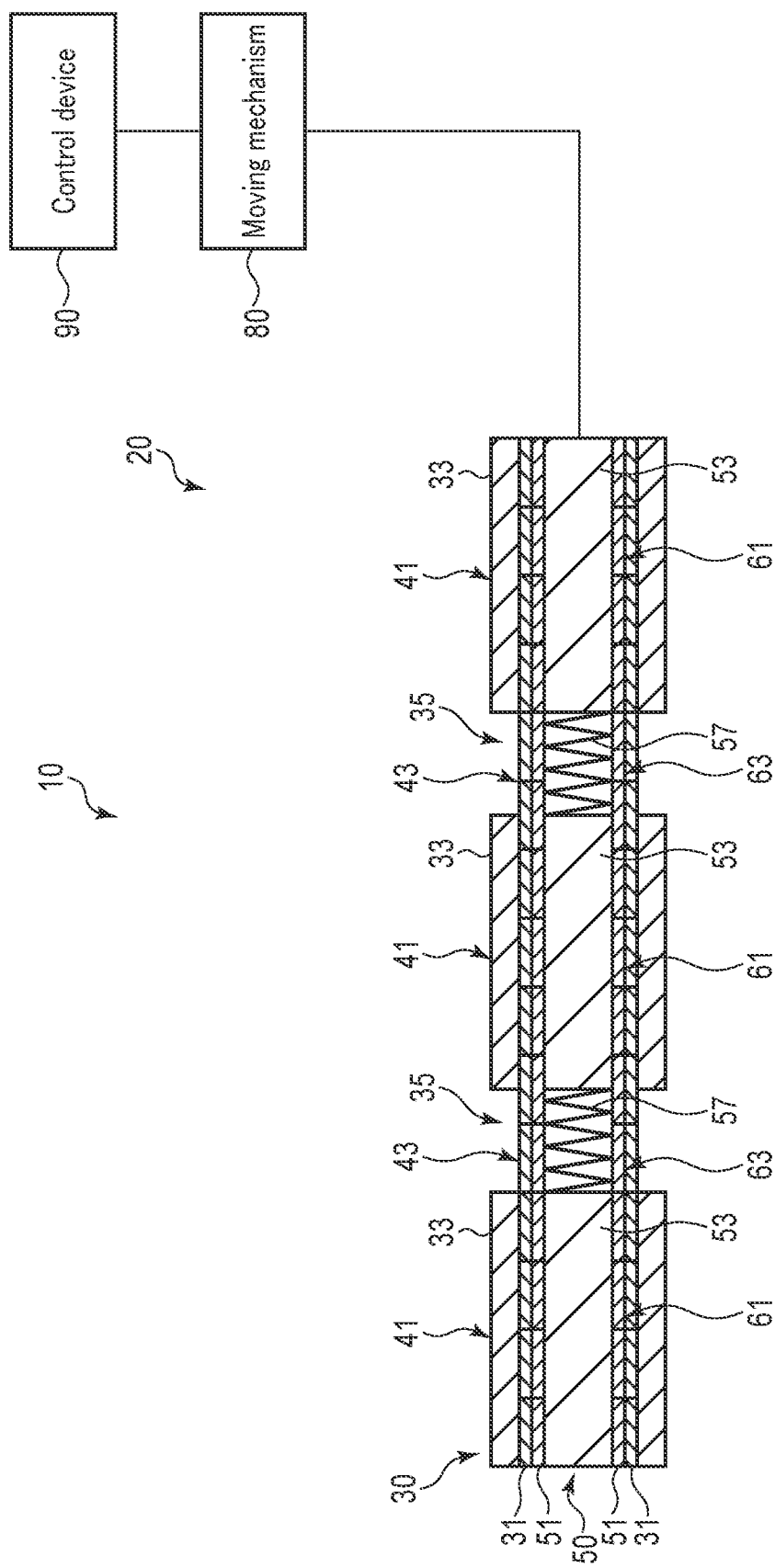
FIG. 1 is a schematic view of a variable stiffness system according to a first embodiment of the present invention, showing that a variable stiffness device of the variable stiffness system is in a low stiffness state.
Figure 2:
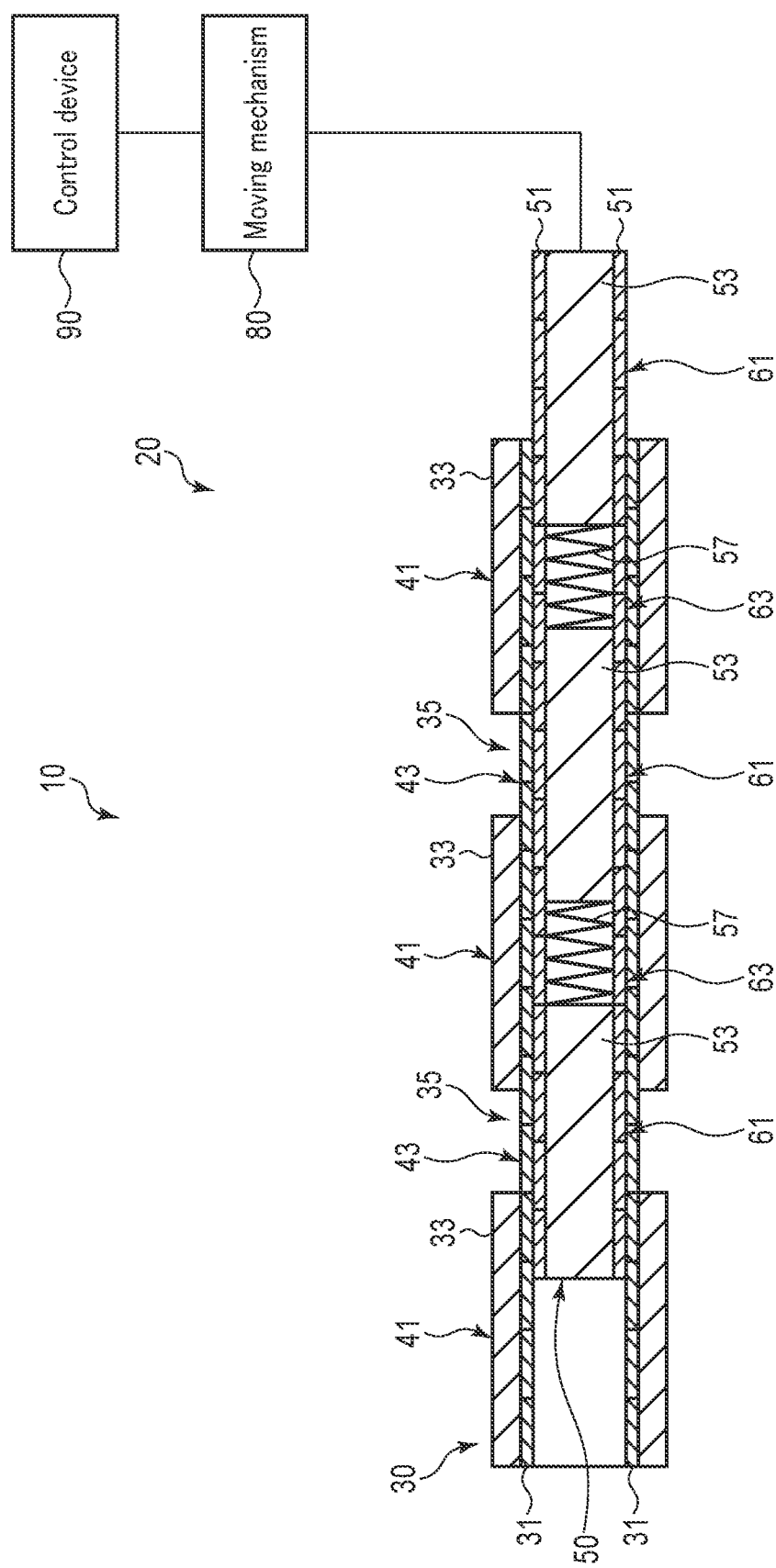
FIG. 2 is a diagram showing that the variable stiffness device shown in FIG. 1 has been switched to a high stiffness state.
Figure 3:
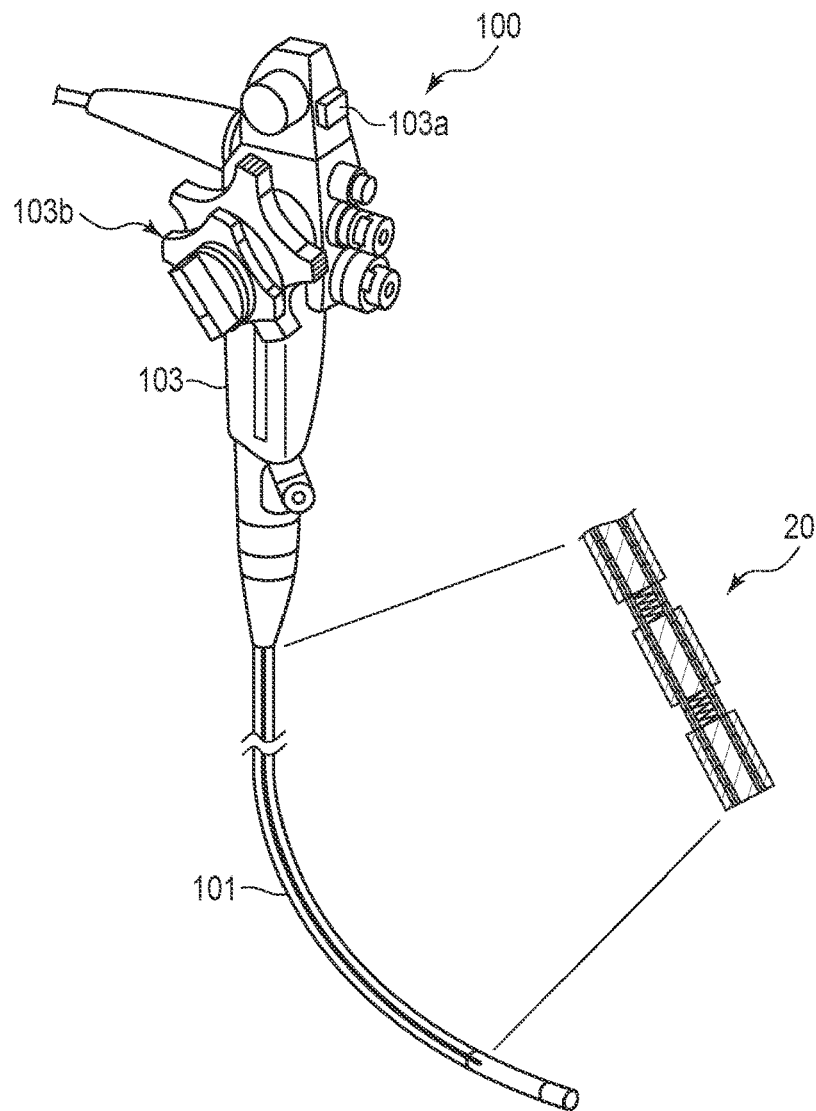
FIG. 3 is a perspective view of an endoscope in which the variable stiffness device is incorporated.

FIG. 1 is a schematic view of a variable stiffness system 10 according to the present embodiment, showing that a variable stiffness device 20 of the variable stiffness system 10 is in a low stiffness state. FIG. 2 is a diagram showing that the variable stiffness device 20 shown in FIG. 1 has been switched to a high stiffness state. FIG. 3 is a perspective view of an endoscope 100 including a flexible member 101 in which the variable stiffness device 20 is installed.

Hereinafter, the longitudinal axis directions of the respective components such as the variable stiffness device 20 are the left-right directions of FIGS. 1 and 2, and are the same directions with respect to each other. The length of each component refers to the dimension in the left-right direction of FIGS. 1 and 2.

As shown in FIGS. 1 and 2, the variable stiffness system 10 includes the variable stiffness device 20 configured to provide the flexible member 101 with different levels of stiffness, a moving mechanism 80 included in the variable stiffness device 20, and a control device 90.

The variable stiffness device 20 includes a first elongated member 30, and a second elongated member 50 movable along the first elongated member 30. The first elongated member 30 is an outer cylinder, and the second elongated member 50 is a core member arranged inside the first elongated member 30. For example, the cross-sectional shape of the outer cylinder perpendicular to the longitudinal axis of the outer cylinder is an annular shape, and the outer periphery of the cross section of the core member perpendicular to the longitudinal axis of the core member is in an annular shape. In this case, the variable stiffness device 20 provides bends in any direction with stable stiffness. The cross-sectional shape of each of the outer cylinder and the core member need not necessarily be an annular shape, and may be another shape such as a C-shape.

In the present embodiment, for example, the first elongated member 30 is positioned and fixed with respect to the flexible member 101.

The first elongated member 30 includes a hollow reinforcement member 31 into which the second elongated member 50 is inserted, and at least one tubular first hard member 33 that is arranged on the outer periphery of the reinforcement member 31 and is shorter than the reinforcement member 31. FIGS. 1 and 2 show an example in which three first hard members 33 are arranged to simplify the illustration; however, the number of the first hard members 33 may be discretionarily set.

The reinforcement member 31 is arranged inside the first hard member 33. The reinforcement member 31 functions as a core member for the first hard member 33. The reinforcement member 31 is a tubular outer support member supporting the first hard member 33. The reinforcement member 31 is, for example, cylindrical.

The reinforcement member 31 covers the second elongated member 50 over the entire length of the second elongated member 50. For example, the length of the reinforcement member 31 is about the same as the length of the second elongated member 50. The reinforcement member 31 may be longer than the second elongated member 50. The reinforcement member 31 guides, along the longitudinal axis direction of the first elongated member 30, the second elongated member 50 configured to move along the longitudinal axis direction of the first elongated member 30 with respect to the first elongated member 30. The reinforcement member 31 is bendable.

Figure 4:
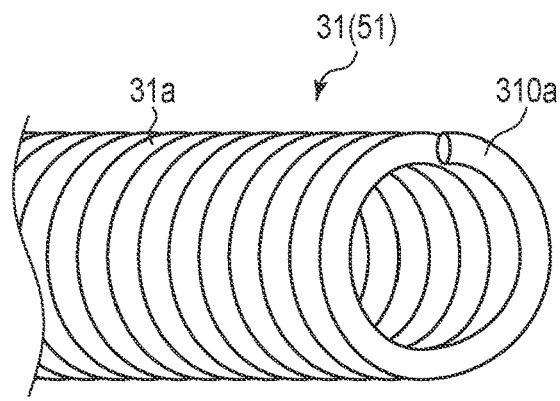
FIG. 4 is a perspective diagram showing an example of a metal reinforcement member of the variable stiffness device shown in FIG. 1.
Figure 5:
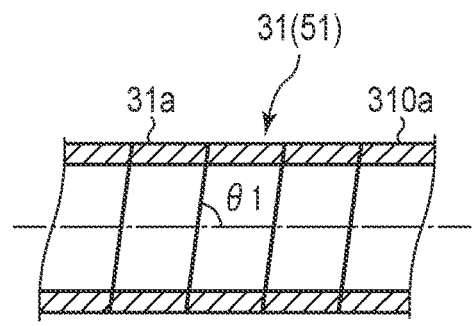
FIG. 5 is a diagram illustrating a winding angle of a first wire of a contact coil, which is the reinforcement member shown in FIG. 4.

The reinforcement member 31 is, for example, a metal material. FIG. 4 is a perspective diagram showing an example of the metal reinforcement member 31. FIG. 5 is a diagram illustrating a winding angle θ1 of the reinforcement member 31 shown in FIG. 4. As shown in FIGS. 4 and 5, the reinforcement member 31 may include, for example, a contact coil 31a. A metal first wire 310a of the contact coil 31a is spirally wound around the longitudinal axis of the reinforcement member 31, and adjacent turns of the first wire 310a are in close contact with each other along the longitudinal axis direction of the reinforcement member 31. An angle formed between the first wire 310a and the longitudinal axis of the reinforcement member 31 is defined as the winding angle θ1 of the first wire 310a. The winding angle θ1 is an angle of inclination of the first wire 310a with respect to the longitudinal axis of the reinforcement member 31. The winding angle θ1 is close to 90° with respect to the longitudinal axis of the reinforcement member 31. In other words, the first wire 310a is arranged substantially perpendicular to the longitudinal axis direction of the reinforcement member 31. Therefore, the reinforcement member 31, which is the metal contact coil 31a, has a high durability that can withstand the compression of the reinforcement member 31 in the longitudinal axis direction of the reinforcement member 31. The reinforcement member 31 having such a feature reinforces the strength of the first elongated member 30 against the compression of the first elongated member 30 in the longitudinal axis direction of the reinforcement member 31.

The first hard member 33 is, for example, cylindrical. The first hard member 33 includes, for example, a metal pipe. The first hard member 33 is a separate member from the reinforcement member 31. The first hard member 33 is shorter than the reinforcement member 31, and the outer peripheral surface of the reinforcement member 31 is exposed to the outside of the first elongated member 30.

The inner peripheral surface of the first hard member 33 is fixed to the outer peripheral surface of the reinforcement member 31 by, for example, bonding or welding. The first hard member 33 is positioned on the reinforcement member 31. The first hard members 33 are not in direct contact with each other in the longitudinal axis direction of the first elongated member 30, but are arranged at a desired distance from each other. In other words, the first hard members 33 partially surround the reinforcement member 31 over the entire length of the reinforcement member 31. Therefore, a first space 35 is arranged between the first hard members 33 in the longitudinal axis direction of the first elongated member 30. No member is arranged in the first space 35. The first hard members 33 and the first spaces 35 are alternately arranged on the outer peripheral surface of the reinforcement member 31 in the longitudinal axis direction of the first elongated member 30. To simplify the illustration, FIGS. 1 and 2 show an example in which two first spaces 35 are arranged.

The length of the first hard member 33 is different from the length of the first space 35. For example, the first hard member 33 is longer than the first space 35. The length of the first hard member 33 may be about the same as or smaller than the length of the first space 35. The lengths of the respective first spaces 35 are about the same. The lengths of the respective first spaces 35 may be different. In the first space 35, the outer peripheral surface of the reinforcement member 31 is exposed to the outside of the first elongated member 30. The first space 35 indicates an outer peripheral side of a portion of the reinforcement member 31 that is not covered with the first hard member 33 along the entire length of the reinforcement member 31. Since the first elongated member 30 is positioned and fixed with respect to the flexible member 101, the first space 35 is positioned and fixed with respect to a desired area of the flexible member 101.

With the reinforcement member 31 and the first hard member 33 described above, the first elongated member 30 includes at least one first high bending stiffness section 41 having a relatively high bending stiffness and at least one first low bending stiffness section 43 having a relatively low bending stiffness. That is, the first high bending stiffness section 41 is formed of the tubular first hard member 33 and a part of the reinforcement member 31, the part being arranged inside the first hard member 33. The first low bending stiffness section 43 is formed of a part of the reinforcement member 31, the part being not arranged inside the first hard member 33, in other words, the part being not covered with the first hard member 33 and being exposed from the first hard member 33. That is, the first low bending stiffness section 43 is formed of a part of the reinforcement member 31, the part being in the first space 35. The reinforcement member 31 is shared by the first high bending stiffness section 41 and the first low bending stiffness section 43.

The reinforcement member 31 is a tubular soft portion having a low bending stiffness, and the first hard member 33 is a tubular hard portion having a high bending stiffness. The first hard member 33 is harder than the reinforcement member 31.

Thus, the bending stiffness of the first high bending stiffness section 41 is high, and the bending stiffness of the first low bending stiffness section 43 is lower than the bending stiffness of the first high bending stiffness section 41. The bending stiffness of the reinforcement member 31 may be about the same as the bending stiffness of the first hard member 33. Therefore, the bending stiffness of the first high bending stiffness section 41 including a part of the reinforcement member 31 and the first hard member 33 is high, and the bending stiffness of the first low bending stiffness section 43 including only the reinforcement member 31 is low. The first elongated member 30 is relatively difficult to bend at the first high bending stiffness section 41, and is relatively easy to bend at the first low bending stiffness section 43.

To simplify the illustration, FIGS. 1 and 2 show an example in which three first high bending stiffness sections 41 and two first low bending stiffness sections 43 are arranged.

The first hard members 33 and the first spaces 35 are alternately arranged. By this arrangement, the first high bending stiffness sections 41 and the first low bending stiffness sections 43 are alternately arranged in the longitudinal axis direction of the reinforcement member 31. Depending on the length of the first hard member 33 and the length of the first space 35, the length of the first high bending stiffness section 41 is larger than the length of the first low bending stiffness section 43. The length of the first high bending stiffness section 41 may be about the same as or smaller than the length of the first low bending stiffness section 43. The first high bending stiffness section 41 and the first low bending stiffness section 43 are arranged along the longitudinal axis direction of the first elongated member 30. The first high bending stiffness section 41 is continuous with the first low bending stiffness section 43 in the longitudinal axis direction of the first elongated member 30.

When the first elongated member 30 is manufactured, the first hard members 33 are positioned by the reinforcement member 31, and the space between the first hard members 33 (the length of the first space 35) is defined. That is, the reinforcement member 31 has an effect of allowing for easily positioning the first high bending stiffness section 41 and the first low bending stiffness section 43 and defining the length of each of the first high bending stiffness section 41 and the first low bending stiffness section 43.

In FIGS. 1 and 2, the first high bending stiffness section 41 (first hard member 33) is arranged at both ends of the first elongated member 30; however, the arrangement need not be limited thereto. The first low bending stiffness section 43 may be arranged at both ends, or it may be that the first high bending stiffness section 41 (first hard member 33) is arranged at one end and that the first low bending stiffness section 43 is arranged at the other end.

The second elongated member 50 is arranged inside the reinforcement member 31. The second elongated member 50 is adjacent to the first elongated member 30. The outer peripheral surface of a later-described tubular member 51 of the second elongated member 50 is in contact with the inner peripheral surface of the reinforcement member 31. The outer peripheral surface of the tubular member 51 is not in contact with the inner peripheral surface of the reinforcement member 31, and a space (not shown) may be formed between the reinforcement member 31 and the tubular member 51.

The second elongated member 50 includes the tubular member 51, at least one second hard member 53, and at least one soft member 57. To simplify the illustration, FIGS. 1 and 2 show an example in which three second hard members 53 and two soft members 57 are arranged; however, the number of these elements may be discretionarily set. The second hard members 53 and the soft members 57 are arranged inside the tubular member 51.

The tubular member 51 functions as a protective member configured to protect the outer peripheral surfaces of the second hard members 53 and the outer peripheral surfaces of the soft members 57 from the inner peripheral surface of the reinforcement member 31. The tubular member 51 is an intervening member that is interposed between the reinforcement member 31 and the second hard members 53 as well as the soft members 57, and prevents the second hard members 53 and the soft members 57 from being in direct contact with the reinforcement member 31. The tubular member 51 is a tubular inner support member supporting the second hard members 53 and the soft members 57. The tubular member 51 is bendable.

The tubular member 51 is, for example, cylindrical. The tubular member 51 is of, for example, a metal material. For example, the configuration of the tubular member 51 is the same as the configuration of the reinforcement member 31 shown in FIGS. 4 and 5. Therefore, the tubular member 51 includes, for example, a contact coil. The tubular member 51 may be of a resin material, a loosely wound coil, or a stranded tube in which metal wires are twisted around each other.

The second hard member 53 is, for example, a solid member, but may be a hollow member. The second hard member 53 is of, for example, a metal material, but may be of a resin material. The second hard member 53 is a separate member from the tubular member 51. The length of the second hard member 53 is smaller than the length of the tubular member 51. The length of the second hard member 53 is preferably larger than the length of the first space 35.

The second hard members 53 are not in direct contact with each other in the longitudinal axis direction of the second elongated member 50, and are arranged at a desired distance from each other. Therefore, a space is arranged between the second hard members 53 in the longitudinal axis direction of the second elongated member 50. In other words, the second hard members 53 are partially arranged inside the tubular member 51 over the entire length of the tubular member 51. To simplify the illustration, FIGS. 1 and 2 show an example in which two spaces are arranged.

The soft member 57 is arranged in each space between the second hard members 53 in the longitudinal axis direction of the second elongated member 50. Therefore, the second hard members 53 and the soft members 57 are alternately arranged inside the tubular member 51 in the longitudinal axis direction of the second elongated member 50. The second hard members 53 and the soft members 57 are arranged along the longitudinal axis direction of the second elongated member 50. The soft members 57 are not in direct contact with each other, and are arranged at a desired distance from each other. The respective soft members 57 between the second hard members 53 are arranged for positioning the second hard members 53. The ends of the soft members 57 are in contact with the ends of the second hard members 53 adjacent to the ends of the soft members 57. The ends of the soft members 57 may be fixed to the ends of the second hard members 53 adjacent to the ends of the soft members 57 by, for example, bonding or welding.

The soft member 57 includes, for example, a spring member. The spring member includes, for example, a loosely wound spring. The spring member may include, for example, a tightly wound spring. The soft member 57 may include, for example, a linear member such as a thin wire, or an elastic member such as rubber. The outer diameter of the winding of the soft member 57 is about the same as the outer diameter of the second hard member 53. The soft member 57 is, for example, bendable. For example, the soft member 57 is softer and is more easily bent than the second hard member 53. The length of the soft member 57 is smaller than the length of the second hard member 53. The length of the soft member 57 is preferably about the same as the length of the first space 35.

In FIGS. 1 and 2, for example, the second hard members 53 are arranged at both ends of the second elongated member 50. The outer peripheral surfaces of the second hard members 53 at both ends are fixed to the inner peripheral surface of the tubular member 51 by, for example, bonding or welding. Thereby, the second hard members 53 other than those arranged at both ends, and the soft members 57 are positioned on the tubular member 51 without being fixed to the tubular member 51. As a matter of course, the outer peripheral surfaces of the second hard members 53 and the soft members 57 may be fixed to the inner peripheral surface of the tubular member 51 by, for example, bonding or welding, so that the second hard members 53 and the soft members 57 are positioned. If the second hard members 53 are fixed to the tubular member 51 by, for example, bonding or welding, the soft members 57 may be omitted.

The second hard members 53 are arranged at both ends of the second elongated member 50; however, the arrangement need not be limited thereto. The soft members 57 may be arranged at both ends, or it may be that the second hard member 53 is arranged at one end and that the soft member 57 is arranged at the other end. Also, if the members arranged at both ends are fixed to the tubular member 51 by, for example, bonding or welding, the members arranged between the two ends need not be fixed to the tubular member 51.

With the tubular member 51, the second hard members 53, and the soft members 57 described above, the second elongated member 50 includes at least one second high bending stiffness section 61 having a relatively high bending stiffness and at least one second low bending stiffness section 63 having a relatively low bending stiffness. That is, the second high bending stiffness section 61 is formed of the second hard member 53 and a part of the tubular member 51, the part covering the second hard member 53. Also, the second low bending stiffness section 63 is formed of the soft member 57 and a part of the tubular member 51, the part covering the soft member 57. The tubular member 51 is shared by the second high bending stiffness section 61 and the second low bending stiffness section 63.

The tubular member 51 and the soft member 57 are soft portions having a low bending stiffness, and the second hard member 53 is a hard portion having a high bending stiffness.

Thus, the bending stiffness of the second high bending stiffness section 61 is high, and the bending stiffness of the second low bending stiffness section 63 is lower than the bending stiffness of the second high bending stiffness section 61. The bending stiffness of the tubular member 51 may be about the same as the bending stiffness of the second hard member 53. Therefore, the bending stiffness of the second high bending stiffness section 61 including a portion of the tubular member 51 and the second hard member 53 is high, and the bending stiffness of the second low bending stiffness section 63 including a part of the tubular member 51 and the soft member 57 is low. The second elongated member 50 is relatively difficult to bend at the second high bending stiffness section 61, and is relatively easy to bend at the second low bending stiffness section 63.

To simplify the illustration, FIGS. 1 and 2 show an example in which three second high bending stiffness sections 61 and two first low bending stiffness sections 63 are arranged.

The second hard members 53 and the soft members 57 are alternately arranged. By this arrangement, the second high bending stiffness sections 61 and the second low bending stiffness sections 63 are alternately arranged in the longitudinal axis direction of the second elongated member 50. Depending on the length of the second hard member 53 and the length of the soft member 57, the length of the second high bending stiffness section 61 is greater than the length of the second low bending stiffness section 63. The length of the second high bending stiffness section 61 may be about the same as or smaller than the length of the second low bending stiffness section 63. The second high bending stiffness section 61 and the second low bending stiffness section 63 are arranged along the longitudinal axis direction of the second elongated member 50. Also, the second high bending stiffness section 61 is continuous with the second low bending stiffness section 63 in the longitudinal axis direction of the second elongated member 50.

When the second elongated member 50 is manufactured, for example, the second hard members 53 and the soft members 57 are positioned by the tubular member 51, and the space between the second hard members 53 is defined. That is, the tubular member 51 exhibits, for example, an effect of allowing for easily positioning the second high bending stiffness section 61 and the second low bending stiffness section 63 and defining the length of each of the second high bending stiffness section 61 and the second low bending stiffness section 63.

In FIGS. 1 and 2, the second high bending stiffness sections 61 (second hard members 53) are arranged at both ends of the second elongated member 50; however, the arrangement need not be limited thereto. The second low bending stiffness sections 63 may be arranged at both ends, or it may be that the second high bending stiffness section 61 is arranged at one end and the second low bending stiffness section 63 is arranged at the other end.

For example, the length of the second hard member 53 is greater than the length of the first space 35. Therefore, the length of the second high bending stiffness section 61 is greater than the length of the first low bending stiffness section 43.

For example, the sum of the bending stiffness of the tubular member 51 and the bending stiffness of the second hard member 53 may be about the same as the sum of the bending stiffness of the reinforcement member 31 and the bending stiffness of the first hard member 33. Therefore, the bending stiffness of the second high bending stiffness section 61 may be about the same as the bending stiffness of the first high bending stiffness section 41. The bending stiffness of the second high bending stiffness section 61 may be higher or lower than the bending stiffness of the first high bending stiffness section 41.

For example, the sum of the bending stiffness of the tubular member 51 and the bending stiffness of the soft member 57 may be about the same as the bending stiffness of the reinforcement member 31. Therefore, the bending stiffness of the second low bending stiffness section 63 may be about the same as the bending stiffness of the first low bending stiffness section 43.

The bending stiffness of the second high bending stiffness section 61 is higher than the bending stiffness of the first low bending stiffness section 43.

The second elongated member 50 moves inside the reinforcement member 31 along the longitudinal axis direction of the reinforcement member 31 to thereby change the position of the second elongated member 50 with respect to the first elongated member 30. Changing the relative position of the first elongated member 30 and the second elongated member 50 causes a variation in the stiffness of a part of the variable stiffness device 20 in the longitudinal axis direction of the variable stiffness device 20. Thereby, the variable stiffness device 20 provides the flexible member 101 with different levels of stiffness.

In order to change the relative position, the moving mechanism 80 moves the second elongated member 50 with respect to the first elongated member 30. When the second elongated member 50 moves, the outer peripheral surface of the tubular member 51 slides on the inner peripheral surface of the reinforcement member 31. The moving mechanism 80 moves the second elongated member 50 by pulling or pushing the second elongated member 50. For example, the tubular member 51 is pulled or pushed. The moving mechanism 80 is electrically connected to the control device 90, and the driving of the moving mechanism 80, that is, the movement of the second elongated member 50 by the moving mechanism 80, is controlled by the control device 90.

The moving mechanism 80 includes, for example, a motor (not shown), and a moving member (not shown) that is connected to one end of the second elongated member 50 and configured to move the second elongated member 50 by a rotational force of the motor. The motor may be driven by an operation such as turning on or off a switch 103a in a control section 103 described later. The moving member is, for example, directly connected to one end of the tubular member 51, and pulls or pushes the second elongated member 50 by a rotational force of the motor. The moving member is arranged from the arrangement position of the motor to one end of the tubular member 51. For example, the moving member is arranged inside the control section 103 and the flexible member 101. The moving member is, for example, a wire-like member. Thus, the moving mechanism 80 is electrically driven.

The control device 90 controls the movement of the second elongated member 50 by the motor of the moving mechanism 80. The control device 90 controls the pulling, pushing, and stopping of the moving mechanism 80 in conjunction with the operation of the switch 103a. The control device 90 is constituted by, for example, a hardware circuit including an ASIC, etc. The control device 90 may be constituted by a CPU. If the control device 90 is constituted by a processor, a program code for causing the processor to function as the control device 90 by executing the program code is stored in an internal memory of the processor or in an external memory (not shown) arranged to be accessible by the processor.

In the moving mechanism 80, the motor may be omitted, and the second elongated member 50 may be moved by a manual operation. For example, the moving mechanism 80 may include a control dial 103b in place of the motor. The control dial 103b is arranged on the control section 103, and is connected to the moving member. For example, the control dial 103b is operated by a finger of a hand gripping the control section 103, and rotated about the central axis of the control dial 103b by the operation. The control dial 103b is switched between the ON position and the OFF position by rotation. In response to the switching, the moving member is pulled or pushed. Thereby, the second elongated member 50 moves. Instead of the control dial 103b, a lever (not shown) may be used. Thus, the moving mechanism 80 is manually driven. In this case, the control device 90 is omitted.

Also, the moving mechanism 80 and the control device 90 may be omitted, and the second elongated member 50 may be moved by a manual operation of an operator who operates the variable stiffness device 20. For example, an end of the second elongated member 50 is held by an operator's hand, and the second elongated member 50 is moved by the pushing and pulling performed by the operator. To hold an end of the second elongated member 50, it is preferable that the second elongated member 50 be longer than the first elongated member 30, and that the end of the second elongated member 50 protrude outward farther than the first elongated member 30 in the longitudinal axis direction of the second elongated member 50. For example, if the first elongated member 30 and the second elongated member 50 are arranged inside the tubular flexible member 101 as described later, an end of the second elongated member 50 may extend to the control section 103, and protrude, for holding, from the inside of the control section 103 to the outside of the control section 103 through a housing section of the control section 103. An end of the second elongated member 50 may protrude to the outside at a proximal end of the flexible member 101. Not only an end of the second elongated member 50 but also a portion to be held may protrude to the outside.

Herein, the relationship between the variable stiffness device 20 and the flexible member 101 will be described.

As shown in FIG. 3, the variable stiffness device 20 is installed in the flexible member 101. The second elongated member 50 and the moving member are not restricted by the flexible member 101. For example, the first elongated member 30, the second elongated member 50, and the moving member are arranged in a limited space of the tubular flexible member 101. The limited space means a space that can just contain the first elongated member 30, the second elongated member 50, and the moving member. Therefore, the first elongated member 30, the second elongated member 50, and the flexible member 101 do not actively deform.

For example, the flexible member 101 is a tube that has an inner diameter slightly larger than the outer diameter of the variable stiffness device 20, particularly the outer diameter of the first hard member 33 due to the arrangement of the variable stiffness device 20, and can be bent by an external force applied to the flexible member 101. The first elongated member 30, the second elongated member 50, and the moving member may be arranged inside the tube. Here, gravity is also considered as part of the external force.

The flexible member 101 is an example of an insertion section of the endoscope 100. The endoscope 100 may be for medical use or for industrial use. The endoscope 100 includes the flexible member 101 and the variable stiffness device 20 that is installed in the flexible member 101 and configured to provide the flexible member 101 with different levels of stiffness. The flexible member 101 may be used, for example, as a manipulator or an elongated member such as a catheter. The motor of the moving mechanism 80 and the control device 90 may be arranged in the control section 103 of the endoscope 100 connected to a proximal end of the insertion section, or may be arranged in a control device (not shown) for the endoscope 100 connected to the endoscope 100. Thus, the variable stiffness system 10 is mounted in the endoscope 100, or mounted in an endoscope system including the endoscope 100 and the control device for the endoscope 100.

Next, switching of the positional state of the second elongated member 50 with respect to the first elongated member 30 will be described.

In the variable stiffness device 20, the positional state of the second elongated member 50 with respect to the first elongated member 30 is changed by the movement of the second elongated member 50. As a result, the state of the variable stiffness device 20 is switched between a first state to provide the flexible member 101 with first stiffness and a second state to provide the flexible member 101 with second stiffness higher than the first stiffness. The first state and the second state are switched by the second elongated member 50 sliding inside the reinforcement member 31.

In the first state shown in FIG. 1, the second low bending stiffness section 63 is positioned at the first low bending stiffness section 43. As a result, the first low bending stiffness section 43 becomes soft, and the entire variable stiffness device 20 becomes relatively soft. At this time, the second high bending stiffness section 61 is arranged on the periphery of the first high bending stiffness section 41, and the second low bending stiffness section 63 is arranged on the periphery of the first low bending stiffness section 43. The periphery of the first high bending stiffness section 41 in the first state refers to a position where the second high bending stiffness section 61 is adjacent to the first high bending stiffness section 41. Specifically, the second high bending stiffness section 61 is arranged inside the first high bending stiffness section 41. The periphery of the first low bending stiffness section 43 in the first state refers to a position where the second low bending stiffness section 63 is adjacent to the first low bending stiffness section 43. Specifically, the second low bending stiffness section 63 is arranged inside the first low bending stiffness section 43.

In the first state described above, the first low bending stiffness section 43 is in a state where it is easily bent, and the first elongated member 30 and the second elongated member 50 are in a low stiffness state where they can be easily deformed according to an external force. In the first state, the variable stiffness device 20 can be easily bent, for example, by an external force. Thus, in the first state, the variable stiffness device 20 provides the flexible member 101 with a relatively low stiffness such that the flexible member 101 is easily bent. Then, the flexible member 101 can be easily bent, for example, by an external force.

Figure 6:
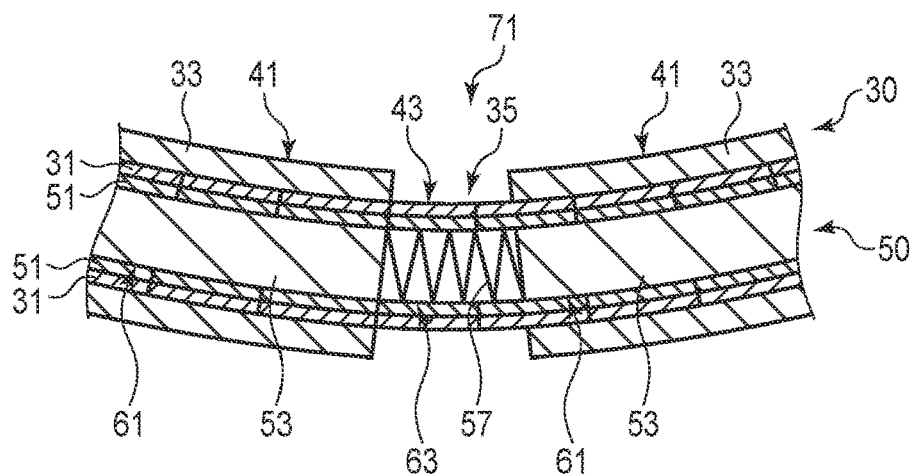
FIG. 6 is a diagram showing that a joint of the variable stiffness device is in a low stiffness state.

Specifically, the first low bending stiffness section 43 is sandwiched between the two first high bending stiffness sections 41 in the longitudinal axis direction of the first elongated member 30. As shown in FIG. 6, the first low bending stiffness section 43 functions as a joint 71 of the variable stiffness device 20 when one of the first high bending stiffness sections 41 is bent with respect to the other of the first high bending stiffness sections 41. Therefore, the joint 71 is easily bent by an external force.

A part of the flexible member 101 in the low stiffness state is easily deformed in accordance with an external force acting on the flexible member 101. Therefore, the flexible member 101 can be easily bent by an external force. When the joint 71 is in the low stiffness state, one of the first high bending stiffness sections 41 is more easily bent with respect to the other first high bending stiffness section 41, than when the joint 71 is in the high stiffness state. That is, the variable stiffness device 20 and the flexible member 101 are more easily bent.

In the first state, the variable stiffness device 20 provides low stiffness to only a part of the flexible member 101 along the entire length of the flexible member 101. Therefore, the flexible member 101 does not switch from the high stiffness state to the low stiffness state over the entire length of the flexible member 101, but partially switches from the high stiffness state to the low stiffness state. In other words, a part of the flexible member 101 along the entire length switches from the high stiffness state to the low stiffness state. Thus, the variable stiffness device 20 changes the stiffness state of the variable stiffness device 20 on the periphery of the first low bending stiffness section 43, which results in a variation in the stiffness of a desired area in the flexible member 101.

In the second state shown in FIG. 2, the second high bending stiffness section 61 is positioned at the first low bending stiffness section 43. As a result, the first low bending stiffness section 43 becomes hard, and the entire variable stiffness device 20 becomes relatively hard. At this time, the second high bending stiffness section 61 is arranged on the periphery of the first low bending stiffness section 43, and the second low bending stiffness section 63 is arranged on the periphery of the first high bending stiffness section 41. The periphery of the first low bending stiffness section 43 in the second state refers to a position where the first low bending stiffness section 43 is adjacent to the second high bending stiffness section 61. Specifically, the first low bending stiffness section 43 covers a large part of the second high bending stiffness section 61. The periphery of the first high bending stiffness section 41 in the second state refers to a position where the second low bending stiffness section 63 is adjacent to the first high bending stiffness section 41. Specifically, the second low bending stiffness section 63 is arranged inside the first high bending stiffness section 41.

In the second state described above, the first low bending stiffness section 43 is in a state where it is difficult to bend, and the first elongated member 30 and the second elongated member 50 are in a high stiffness state of having a stiffness higher than that in the low stiffness state. In the second state, the variable stiffness device 20 can, for example, maintain an about linear state or be more gently bent by an external force than in the first state. Therefore, in the second state, the variable stiffness device 20 takes a high stiffness state with a tendency for the flexible member 101 to have a shape that causes the flexible member 101 to be difficult to bend against an external force. The shape that causes the flexible member 101 to be difficult to bend may be, for example, linear. The variable stiffness device 20 provides the flexible member 101 with a relatively high stiffness, and the flexible member 101 can, for example, maintain an about linear state or be more gently bent by an external force than in the first state.

Figure 7:
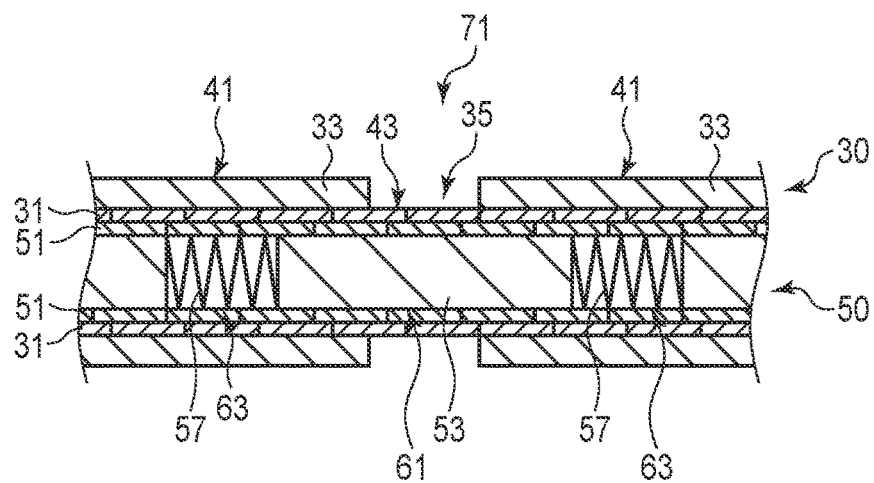
FIG. 7 is a diagram showing that the joint of the variable stiffness device is in a high stiffness state.

Specifically, when the first low bending stiffness section 43 covers the second high bending stiffness section 61 as shown in FIG. 7, the joint 71 also switches from the low stiffness state to the high stiffness state. Therefore, when the joint 71 is in the high stiffness state, one of the first high bending stiffness sections 41 is more difficult to bend with respect to the other first high bending stiffness section 41 than when the joint 71 is in the low stiffness state, and maintains an about linear state. That is, the variable stiffness device 20 is more difficult to bend and maintains an about linear state.

The first high bending stiffness sections 41 and the second high bending stiffness sections 61 are continuously and alternately arranged in the longitudinal axis direction of the variable stiffness device 20. As a result, the variable stiffness device 20 takes a high stiffness state over the entire length. The variable stiffness device 20 provides the flexible member 101 with relatively high stiffness such that the flexible member 101 is difficult to bend.

A part of the flexible member 101 in the high stiffness state counteracts an external force acting on the flexible member 101, that is, a force that may deform the second high bending stiffness section 61. Therefore, a part of the flexible member 101 in the high stiffness state maintains an about linear state.

In the second state, the variable stiffness device 20 provides high stiffness to only a part of the flexible member 101 along the entire length of the flexible member 101. Therefore, the flexible member 101 does not switch from the low stiffness state to the high stiffness state over the entire length of the flexible member 101, but partially switches from the low stiffness state to the high stiffness state. In other words, a part of the flexible member 101 along the entire length switches from the low stiffness state to the high stiffness state. Thus, the variable stiffness device 20 changes the stiffness state of the variable stiffness device 20 on the periphery of the first low bending stiffness section 43, which results in a variation in the stiffness of a desired area in the flexible member 101.

Next, the variation in the stiffness of the flexible member 101 accompanying the switching of the positional state will be described.

First, the variable stiffness system 10 is in the first state, which is an initial state, as shown in FIG. 1. At this time, the first elongated member 30 and the second elongated member 50 are in the low stiffness state over the entire length.

If the switch 103a in the control section 103 is turned on, the control device 90 controls the moving mechanism 80 so that the positional state switches from the first state to the second state. That is, the moving mechanism 80 moves the second elongated member 50 with respect to the first elongated member 30, as shown in FIG. 2, so that the positional state switches from the first state to the second state.

If the switch 103a in the control section 103 is turned off, the control device 90 controls the moving mechanism 80 so that the positional state switches from the second state to the first state. That is, the moving mechanism 80 moves the second elongated member 50 with respect to the first elongated member 30, as shown in FIG. 1, so that the positional state switches from the second state to the first state.

By switching the positional state between the first state and the second state using the moving mechanism 80 as described above, the stiffness of a desired area in the flexible member 101 is switched.

In the present embodiment, the stiffness of a part of the variable stiffness device 20 in the longitudinal axis direction of the variable stiffness device 20 can be varied by the movement of the second elongated member 50 with respect to the first elongated member 30. In the present embodiment, the variation in the stiffness of a part can vary the stiffness of a desired area in the flexible member 101, and can partially vary the stiffness state of the flexible member 101. In the present embodiment, the first high bending stiffness sections 41 and the first low bending stiffness sections 43 are alternately arranged, and the second elongated member 50 moves inside the reinforcement member 31 of the first elongated member 30. Thereby, the configuration of the variable stiffness device 20 can be simple and thin. As a result, the flexible member 101 becomes thin. Thus, in the present embodiment, it is possible to provide the variable stiffness device 20 having a simple configuration and capable of providing different levels of stiffness to the flexible member 101 as an installation target, and the endoscope 100 including the variable stiffness device 20. In the present embodiment, it is possible to provide the variable stiffness device 20 that can easily adopt the configuration in which the flexible member 101 does not easily become thick.

In the present embodiment, the reinforcement member 31 not only functions as an exclusive member for guiding the second elongated member 50, but also functions as the first high bending stiffness sections 41 and the first low bending stiffness sections 43 by being shared by the first high bending stiffness sections 41 and the first low bending stiffness sections 43. Therefore, in the present embodiment, the number of components of the first elongated member 30 can be reduced.

In the present embodiment, when the first elongated member 30 is manufactured, the reinforcement member 31 allows easily positioning the first hard members 33 and easily defining the length of the first space 35. Therefore, the first high bending stiffness sections 41 and the first low bending stiffness sections 43 can be easily positioned, and the length of each of the first high bending stiffness sections 41 and the first low bending stiffness sections 43 can be easily defined. Also, in the present embodiment, the first elongated member 30 can be easily built by the reinforcement member 31.

In the present embodiment, since the second elongated member 50 is inserted into the first elongated member 30, the variable stiffness device 20 can be made thin, and the flexible member 101 can be made thin.

In the present embodiment, the tubular member 51 not only functions as an exclusive member for protecting the second hard members 53 and the soft members 57 from the reinforcement member 31, but also functions as the second high bending stiffness sections 61 and the second low bending stiffness sections 63 by being shared by the second high bending stiffness sections 61 and the second low bending stiffness sections 63. Therefore, in the present embodiment, the number of components of the second elongated member 50 can be reduced.

In the present embodiment, the tubular member 51 can prevent abrasion of the second hard members 53 and the soft members 57 against the reinforcement member 31.

In the present embodiment, when the second elongated member 30 is manufactured, the second hard members 53 and the soft members 57 can be easily positioned by the tubular member 51. Therefore, the second high bending stiffness sections 61 and the second low bending stiffness sections 63 can be easily positioned, and the length of each of the second high bending stiffness sections 61 and the second low bending stiffness sections 63 can be easily defined. Also, in the present embodiment, the second elongated member 50 can be easily built by the tubular member 51.

In the present embodiment, the moving mechanism 80 moves the second elongated member 50 with respect to the first elongated member 30. Therefore, in the present embodiment, the positional state can be quickly switched between the first state and the second state, which can achieve a high responsiveness in switching of the stiffness state of the flexible member 101.

In the present embodiment, the first elongated member 30 is positioned and fixed with respect to the flexible member 101, and the second elongated member 50 is moved by the moving mechanism 80; however, the present embodiment need not be limited thereto. It suffices if one of the first elongated member 30 or the second elongated member 50 is moved by the moving mechanism 80.

In addition to the switching of the stiffness, under a circumstance where an external force other than gravity is exerted on the flexible member 101, the variable stiffness device 20 also functions as a bidirectional actuator configured to switch the shape of the flexible member 101. Also, under a circumstance where no external force other than gravity is exerted on the flexible member 101 and the variable stiffness device 20 is in the second state, the variable stiffness device 20 also functions as a unidirectional actuator configured to restore the shape of the flexible member 101 to the original shape.

Now, a comparative example of the present embodiment will be described with reference to FIGS. 8, 9, and 10. In the comparative example, the material of the reinforcement member 31 of the first elongated member 30 is changed from a metal material to a resin material. Namely, the configuration of the comparative example is the same as the configuration of the first embodiment except that a reinforcement member 231 formed of a resin material is employed.

Since the reinforcement member 231 is a soft member made of a resin material, for example, the strength (durability) of the reinforcement member 231 in the longitudinal axis direction of the reinforcement member 231 is inferior to the strength of the reinforcement member 31 made of a metal material. The strength has a particularly large influence on the bent reinforcement member 231.

Figure 9:
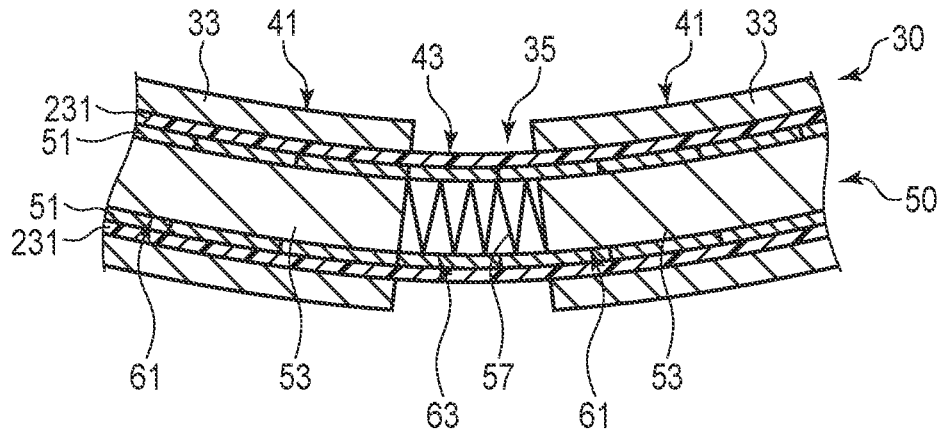
FIG. 9 is a diagram showing that the variable stiffness device shown in FIG. 8 is bent in a low stiffness state.
Figure 10:
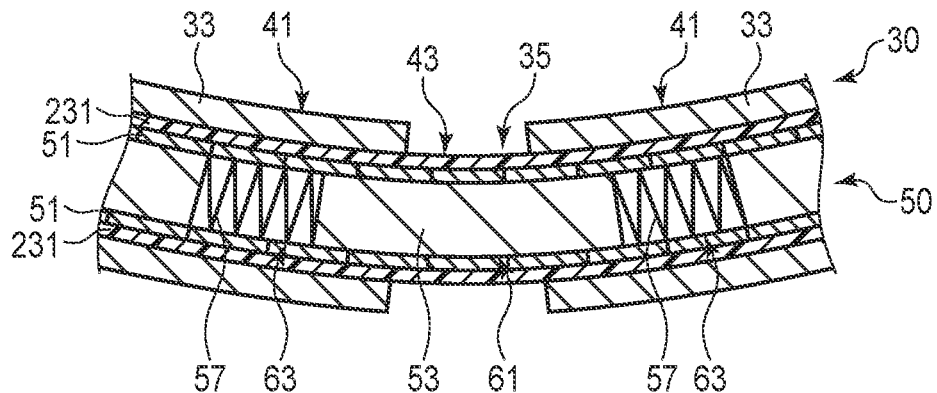
FIG. 10 is a diagram showing that the variable stiffness device shown in FIG. 8 is bent in a high stiffness state.

Let us assume that, in a state where an end 30a of the first elongated member 30 is fixed, and the first elongated member 30 and the second elongated member 50 are bent as shown in FIG. 9, the second elongated member 50 moves toward the right side of the sheet of FIG. 9 with respect to the first elongated member 30, and the positional state of the second elongated member 50 switches from the first state shown in FIG. 9 to the second state shown in FIG. 10.

At this time, a load is applied to the first elongated member 30 by the moving second elongated member 50. The load acts on the first elongated member 30 as a compressive force from the other end 30b of the first elongated member 30, which is a free end, toward the end 30a of the first elongated member 30, which is a fixed end, in the longitudinal axis direction of the first elongated member 30.

Since the first hard member 33 made of a metal material is fixed to the reinforcement member 231 in the first high bending stiffness section 41, the influence of the compressive force applied to the reinforcement member 231 of the first high bending stiffness section 41 is negligible.

The first low bending stiffness section 43 includes only the reinforcement member 231 made of a resin material (soft member). Therefore, when a compressive force is applied to the reinforcement member 231 of the first low bending stiffness section 43, the reinforcement member 231 may be crushed by the compressive force and broken. When the reinforcement member 231 is broken, the first high bending stiffness section 41 and the first low bending stiffness section 43 may be displaced with respect to the second high bending stiffness section 61 and the second low bending stiffness section 63 in each of the first and second states. Thus, even in the second state, the variable stiffness device 20 cannot provide a high stiffness to only a part of the flexible member 101 along the entire length of the flexible member 101, which may cause a case where the variable stiffness device 20 and the flexible member 101 are not difficult to bend and cannot maintain an about linear state. Also, even in the first state, the variable stiffness device 20 cannot provide low stiffness to only a part of the flexible member 101 along the entire length of the flexible member 101, and the variable stiffness device 20 and the flexible member 101 cannot be easily bent. Thus, the variable stiffness device 20 may not operate stably.

In contrast, in the present embodiment described above, the contact coil 31a, which is the metal reinforcement member 31, has a high durability that can withstand compression. Therefore, the durability of the first elongated member 30 is improved against the load applied to the first elongated member 30 in the longitudinal axis direction of the first elongated member 30. Specifically, the strength of the first elongated member 30 is reinforced against the compression of the first elongated member 30, which is a load applied to the first elongated member 30 in the longitudinal axis direction of the first elongated member 30.

As a result, even if a compressive force is applied to the contact coil 31a, it is possible to prevent the first low bending stiffness section 43 from being crushed and damaged by the compressive force. Also, it is possible to prevent the first high bending stiffness section 41 and the first low bending stiffness section 43 from being displaced with respect to the second high bending stiffness section 61 and the second low bending stiffness section 63, and to stably operate the variable stiffness device 20. In addition, since the reinforcement member 31 is made of a metal material, abrasion of the reinforcement member 31 caused by the movement of the second elongated member 50 can be suppressed as compared to the case where the reinforcement member 31 is made of a resin material. Thus, the mechanical strength of the first elongated member 30 can be improved.

In the present embodiment, the second elongated member 50 can be smoothly moved with the reinforcement member 31 serving as a guide, and the stiffness of a desired area in the flexible member 101 can be quickly changed.

Modifications

Hereinafter, modifications of the second elongated member 50 of the present embodiment will be described. The configurations of the respective modifications of the second elongated member 50 can be combined with the configurations of second, third, and fourth embodiments described later and the configurations of the modifications of these embodiments.

Figure 11:
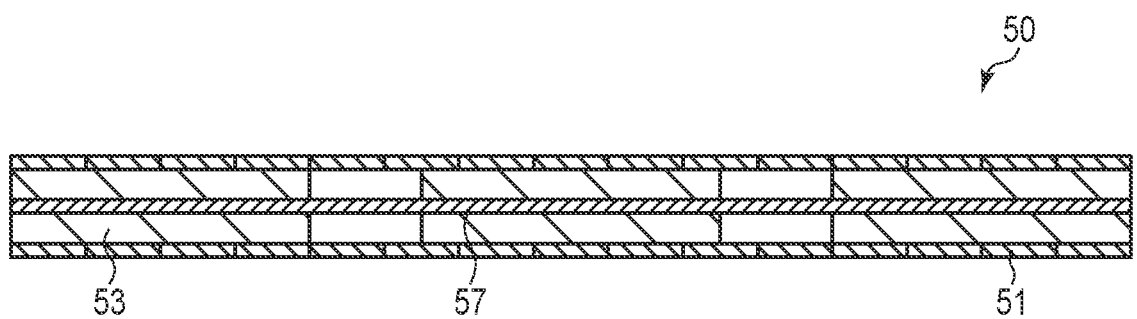
FIG. 11 is a diagram showing a first modification of a second elongated member of the first embodiment.

As a first modification shown in FIG. 11, the second hard member 53 has a tubular shape, for example, a cylindrical shape. The second hard members 53 are not in direct contact with each other in the longitudinal axis direction of the second elongated member 50, and are arranged at a desired distance from each other. Therefore, a space is arranged between the second hard members 53 in the longitudinal axis direction of the second elongated member 50. The soft member 57 includes a wire that passes through each of the second hard members 53. The wire is, for example, a metal. The outer peripheral surface of the wire is fixed to the inner peripheral surfaces of the second hard members 53. Therefore, the second hard members 53 and the outer peripheral surface of the wire exposed from the second hard members 53 are alternately arranged. With the second elongated member 50 having such a configuration, the second elongated member 50 can be easily assembled.

Figure 12:
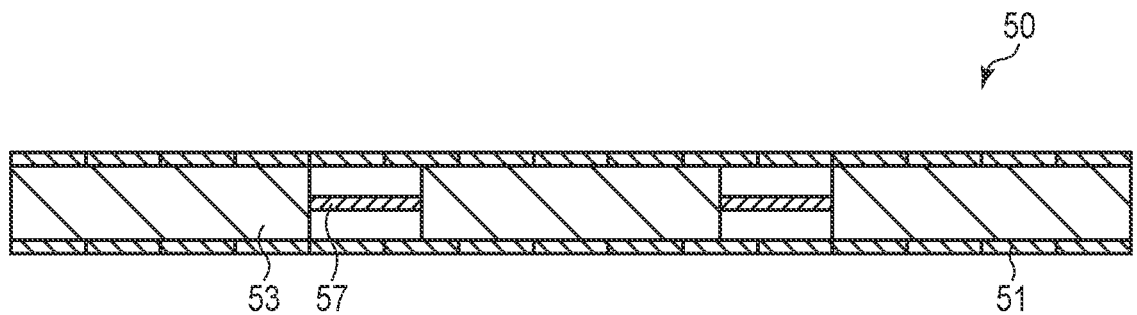
FIG. 12 is a diagram showing a second modification of the second elongated member of the first embodiment.

As a second modification shown in FIG. 12, the soft member 57 may include a wire arranged between the second hard members 53 and connecting the second hard members 53. The wire is, for example, a metal. In this case, the ends of the wire are fixed to the ends of the second hard members 53 adjacent to the ends of the wire by, for example, bonding or welding.

Figure 13:
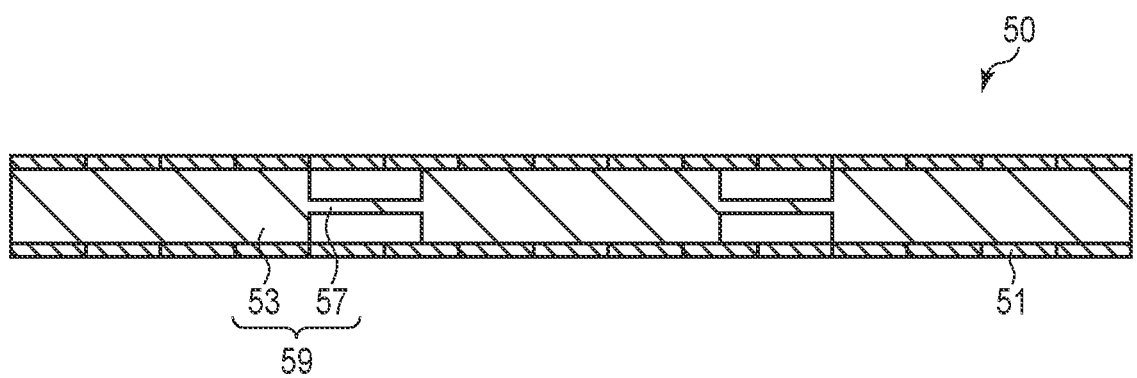
FIG. 13 is a diagram showing a third modification of the second elongated member of the first embodiment.

As a third modification shown in FIG. 13, the second elongated member 50 may include a linear member 59. The linear member 59 is, for example, a metal such as stainless steel. A processed portion of the linear member 59 functions as the soft member 57, and an unprocessed portion of the linear member 59 functions as the second hard member 53. The processing may involve cutting to reduce the diameter of the linear member 59, or formation of many adjacent grooves extending over the entire perimeter. Also, the grooves or cut portions formed in the linear member 59 need not necessarily be formed over the entire perimeter of the linear member, and may be formed partially in the circumferential direction, for example. The soft member 57 is integrated with the second hard members 53 that are thicker than the soft member 57. The second elongated member 50 having such a configuration allows omitting building the second hard members 53 and the soft member 57.

Figure 14:
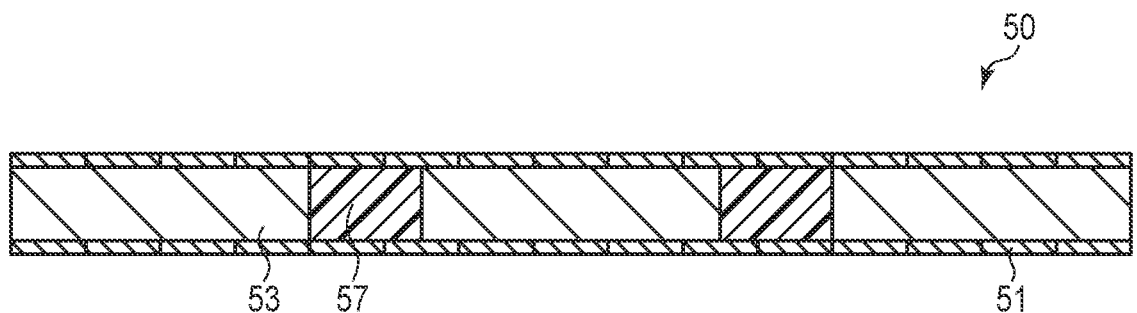
FIG. 14 is a diagram showing a fourth modification of the second elongated member of the first embodiment.

As a fourth modification shown in FIG. 14, the soft member 57 may include a soft resin material. The resin material may have a pillar shape (e.g., columnar shape) or a tubular shape (e.g., cylindrical shape). The thickness of the soft member 57 is about the same as the thickness of the second hard member 53. It suffices if the soft member 57 is arranged between the second hard members 53 in the longitudinal axis direction of the second elongated member 50.

Second Embodiment

Figure 15:
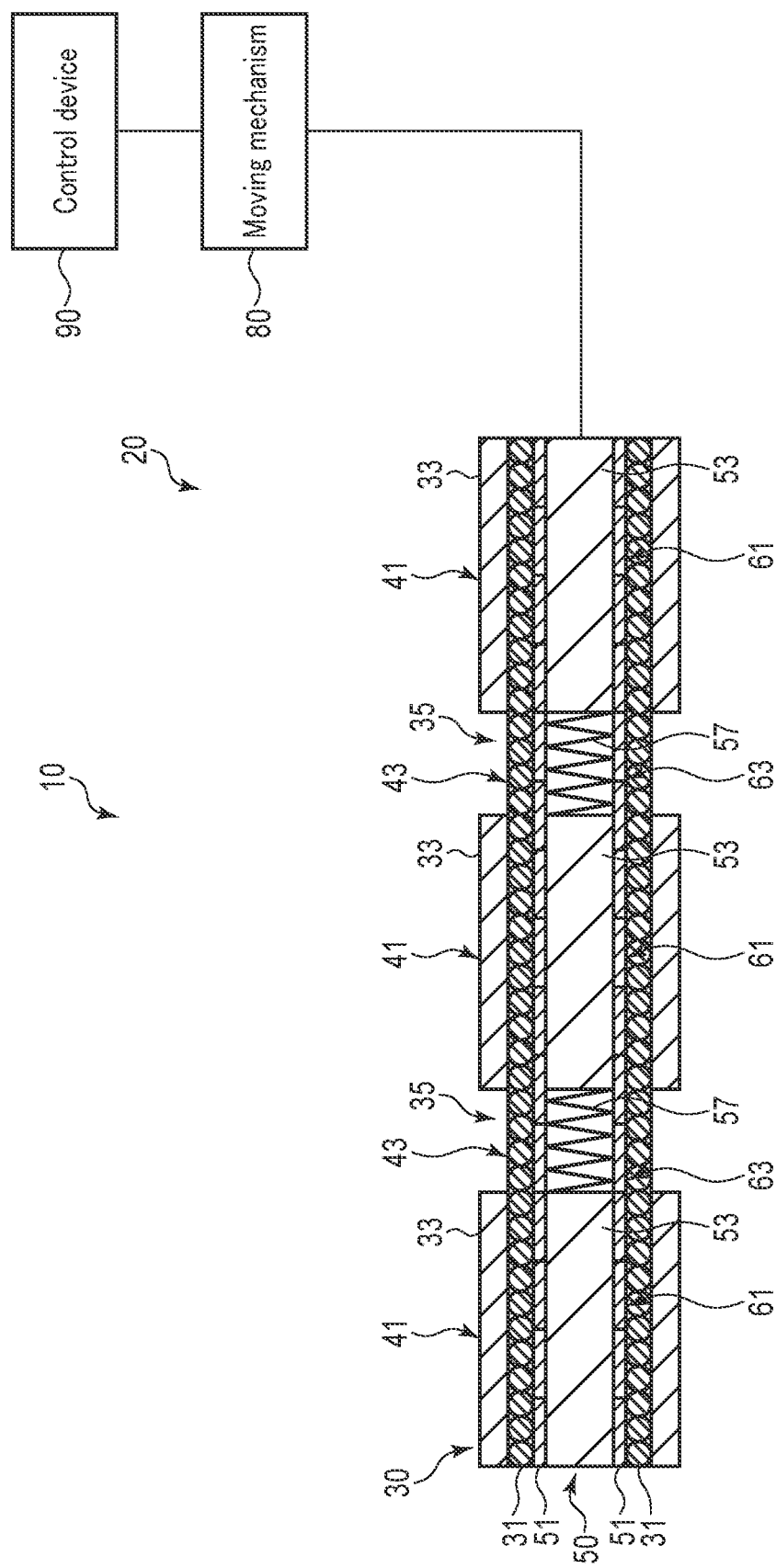
FIG. 15 is a schematic view of a variable stiffness system according to a second embodiment of the present invention.

Hereinafter, the second embodiment of the present invention will be described with reference to FIGS. 15 and 16. FIG. 15 is a schematic view of a variable stiffness system according to the second embodiment of the present invention. FIG. 16 is a diagram showing an example of the metal reinforcement member shown in FIG. 15. In the present embodiment, only the differences from the first embodiment will be described.

The reinforcement member 31 may include, for example, a stranded tube 31b in which metal second wires 310b are twisted around each other. The outer peripheral surface of the stranded tube 31b is fixed to the inner peripheral surfaces of the first hard members 33 covering the outer peripheral surface by, for example, bonding or welding. An angle formed between the second wire 310b and the longitudinal axis of the reinforcement member 31 is defined as the winding angle θ2 of the second wire 310b. The winding angle θ2 is an angle of inclination of the second wire 310b with respect to the longitudinal axis of the reinforcement member 31. The orientation of the second wire 310b indicated by the winding angle 92 is closer to the longitudinal axis of the reinforcement member 31 than the direction orthogonal to the longitudinal axis of the reinforcement member 31. In other words, the second wire 310b is arranged substantially in parallel to the longitudinal axis direction of the reinforcement member 31. Therefore, the reinforcement member 31 as the metal stranded tube 31b has a high durability that can withstand the tension (stretch) of the reinforcement member 31 in the longitudinal axis direction of the reinforcement member 31. The reinforcement member 31 having such a feature reinforces the strength of the first elongated member 30 against the tension of the first elongated member 30 in the longitudinal axis direction of the reinforcement member 31.

Figure 8:
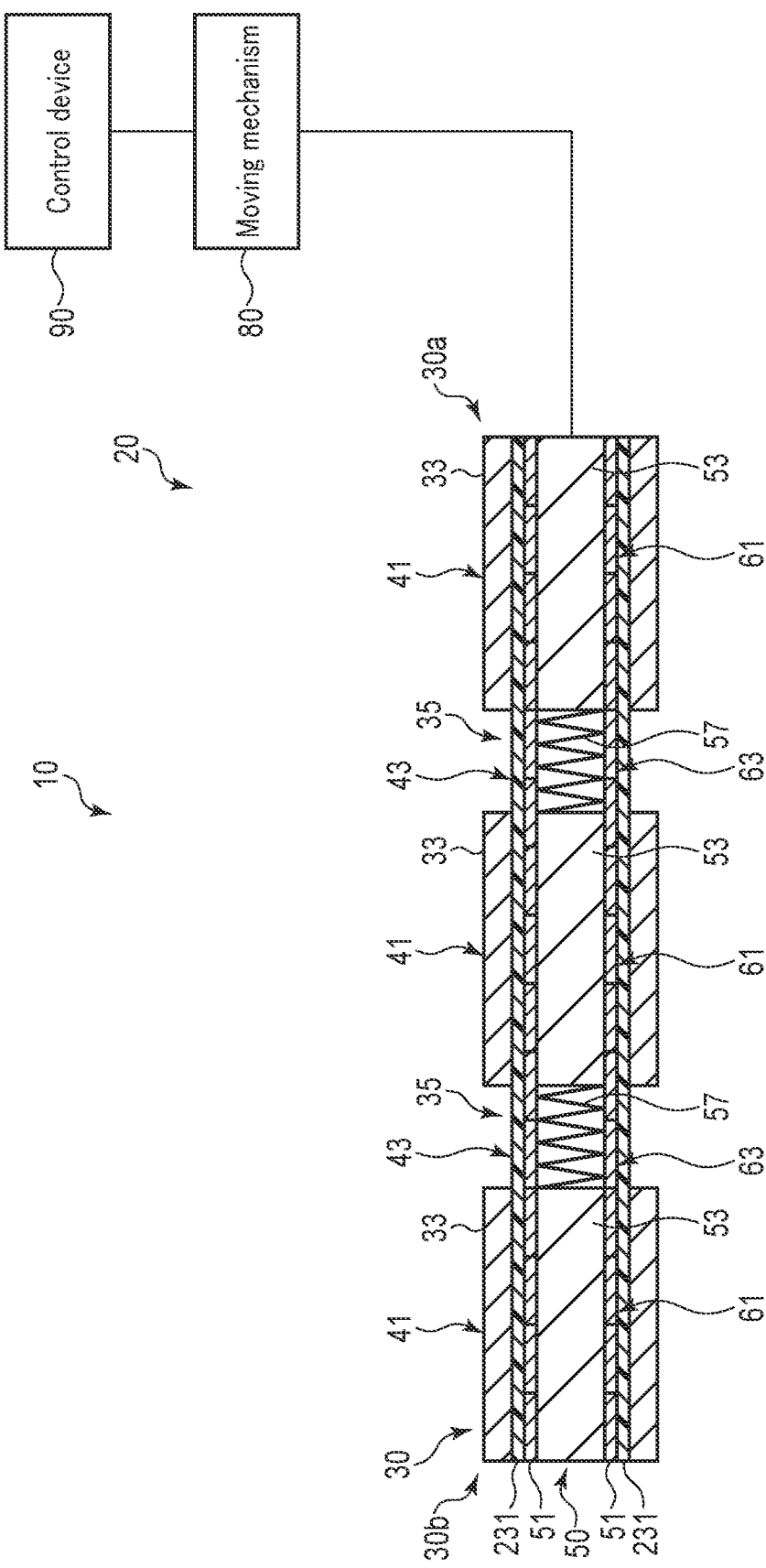
FIG. 8 is a diagram showing a comparative example of the first embodiment in which the reinforcement member is a resin material.

Let us assume that, in a state where the end 30a of the first elongated member 30 is fixed, and the first elongated member 30 and the second elongated member 50 are bent in the comparative example shown in FIGS. 8, 9, and 10, the second elongated member 50 moves toward the left side of the sheet of FIG. 10 with respect to the first elongated member 30, and the positional state of the second elongated member 50 switches from the second state shown in FIG. 10 to the first state shown in FIG. 9.

At this time, a load is applied to the first elongated member 30 by the moving second elongated member 50. The load acts on the first elongated member 30 as a tensile force from the end 30a of the first elongated member 30, which is a fixed end, to the other end 30b of the first elongated member 30, which is a free end, in the longitudinal axis direction of the first elongated member 30.

The first low bending stiffness section 43 includes only a reinforcement member 231 made of a resin material (soft member). Therefore, when a tensile force is applied to the reinforcement member 231 of the first low bending stiffness section 43, the reinforcement member 231 may be stretched by the tensile force and broken. When the reinforcement member 231 is broken, the first high bending stiffness section 41 and the first low bending stiffness section 43 may be displaced with respect to the second high bending stiffness section 61 and the second low bending stiffness section 63 in each of the first and second states.

In the present embodiment, the stranded tube 31b, which is the metal reinforcement member 31, has a high durability that can withstand tension. Therefore, the durability of the first elongated member 30 is improved against the load applied to the first elongated member 30 in the longitudinal axis direction of the first elongated member 30. Specifically, the strength of the first elongated member 30 is reinforced against the tension of the first elongated member 30, which is a load applied to the first elongated member 30 in the longitudinal axis direction of the first elongated member 30.

As a result, even if a tensile force is applied to the stranded tube 31b, it is possible to prevent the first low bending stiffness section 43 from being stretched and broken by the tensile force. Also, it is possible to prevent the first high bending stiffness section 41 and the first low bending stiffness section 43 from being displaced with respect to the second high bending stiffness section 61 and the second low bending stiffness section 63, and to stably operate the variable stiffness device 20.

The thinner the stranded tube 31b (the smaller the outer diameter of the stranded tube 31b), the softer the stranded tube 31b. Therefore, the first elongated member 30 having the stranded tube 31b arranged inside the first hard member 33 can be softened. The second wire 310b is arranged substantially in parallel to the longitudinal axis direction of the reinforcement member 31. Therefore, when the second elongated member 50 (tubular member 51) slides on the inner peripheral surface of the reinforcement member 31 (stranded tube 31b), the sliding resistance of the reinforcement member 31 with respect to the second elongated member 50 is reduced, allowing the second elongated member 50 to slide smoothly.

Third Embodiment

Figure 17:
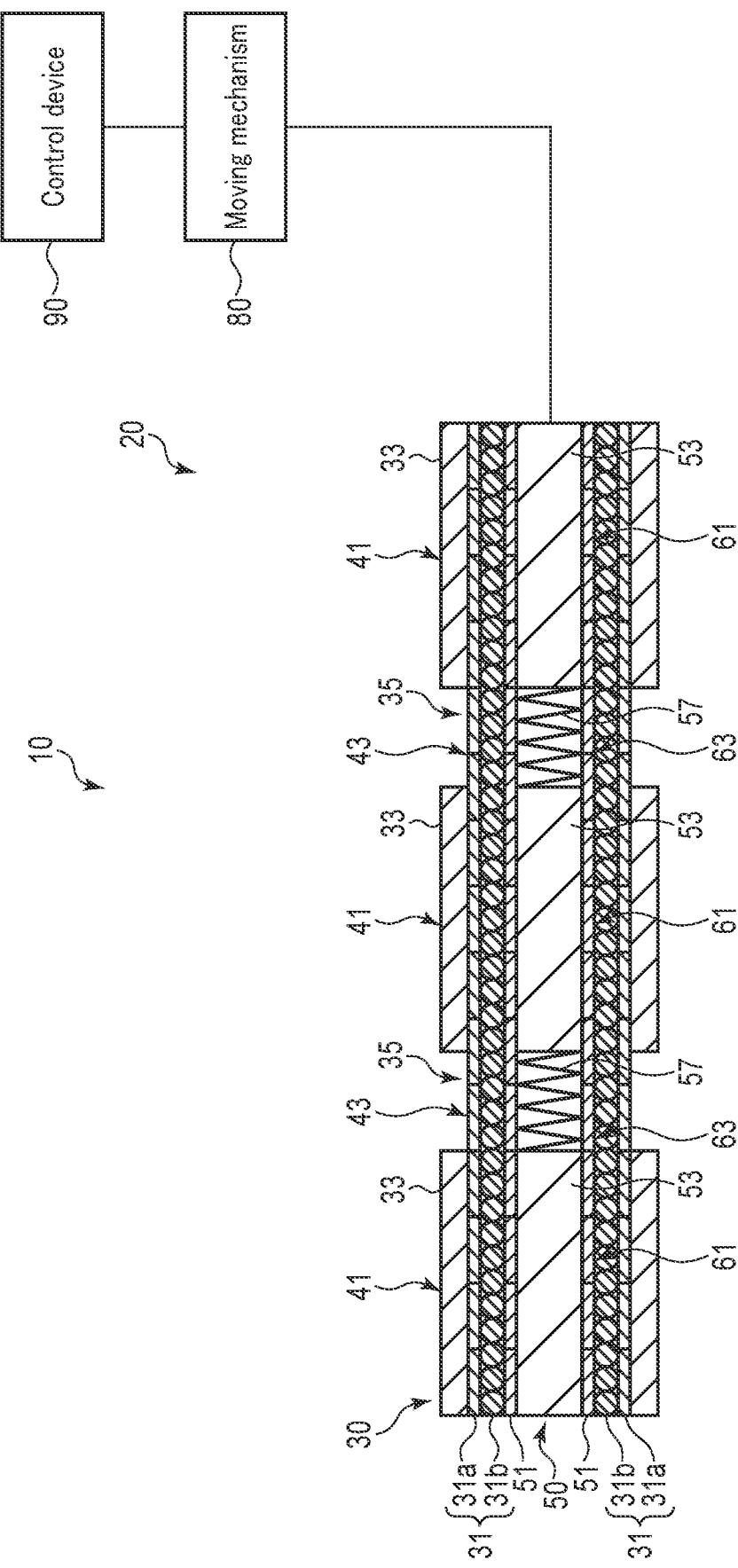
FIG. 17 is a schematic view of a variable stiffness system according to a third embodiment of the present invention.

Hereinafter, the third embodiment of the present invention will be described with reference to FIG. 17. FIG. 17 is a schematic view of a variable stiffness system according to the third embodiment of the present invention. In the present embodiment, only the differences from the first and second embodiments will be described.

The reinforcement member 31 includes the contact coil 31a described in the first embodiment and the stranded tube 31b described in the second embodiment. In the first elongated member 30 of the present embodiment, the first hard member 33, the contact coil 31a, and the stranded tube 31b are arranged in the mentioned order from the outside of the first elongated member 30 toward the inside of the first elongated member 30. Therefore, the stranded tube 31b is arranged on the innermost layer of the first elongated member 30. The stranded tube 31b guides, along the longitudinal axis direction of the first elongated member 30, the second elongated member 50 configured to move along the longitudinal axis direction of the first elongated member 30 with respect to the first elongated member 30.

The contact coil 31a is arranged inside the first hard member 33. The outer peripheral surface of the contact coil 31a is fixed to the inner peripheral surfaces of the first hard members 33 by, for example, bonding or welding.

The stranded tube 31b is arranged inside the contact coil 31a, and the outer peripheral surface of the stranded tube 31b is covered with the contact coil 31a. The outer peripheral surfaces of both ends of the stranded tube 31b are fixed to the inner peripheral surfaces of both ends of the contact coil 31a by, for example, bonding or welding.

The first high bending stiffness section 41 includes the first hard member 33, a part of the contact coil 31a, the part being arranged inside the first hard member 33, and a part of the stranded tube 31b, the part being arranged inside the contact coil 31a.

The first low bending stiffness section 43 includes a part of the contact coil 31a and a part of the stranded tube 31b, the part being not arranged inside the first hard member 33, in other words, the part being not covered with the first hard member 33 and being exposed from the first hard member 33.

In the present embodiment, both of the effects of the first embodiment and the second embodiment can be obtained by way of the contact coil 31a and the stranded tube 31b. That is, even if a compressive force is applied to the contact coil 31a, the contact coil 31a can prevent the first low bending stiffness section 43 from being crushed and broken by the compressive force, and even if a tensile force is applied to the stranded tube 31b, the stranded tube 31b can prevent the first low bending stiffness section 43 from being stretched and broken by the tensile force.

Since the first low bending stiffness section 43 includes both the stranded tube 31b and the contact coil 31a, the strength of the first low bending stiffness section 43 can be improved.

Since both ends of the stranded tube 31b are fixed, the movement of the stranded tube 31b with respect to the first hard member 33 in the longitudinal axis direction of the first elongated member 30 can be regulated.

First Modification of Third Embodiment

Figure 18:
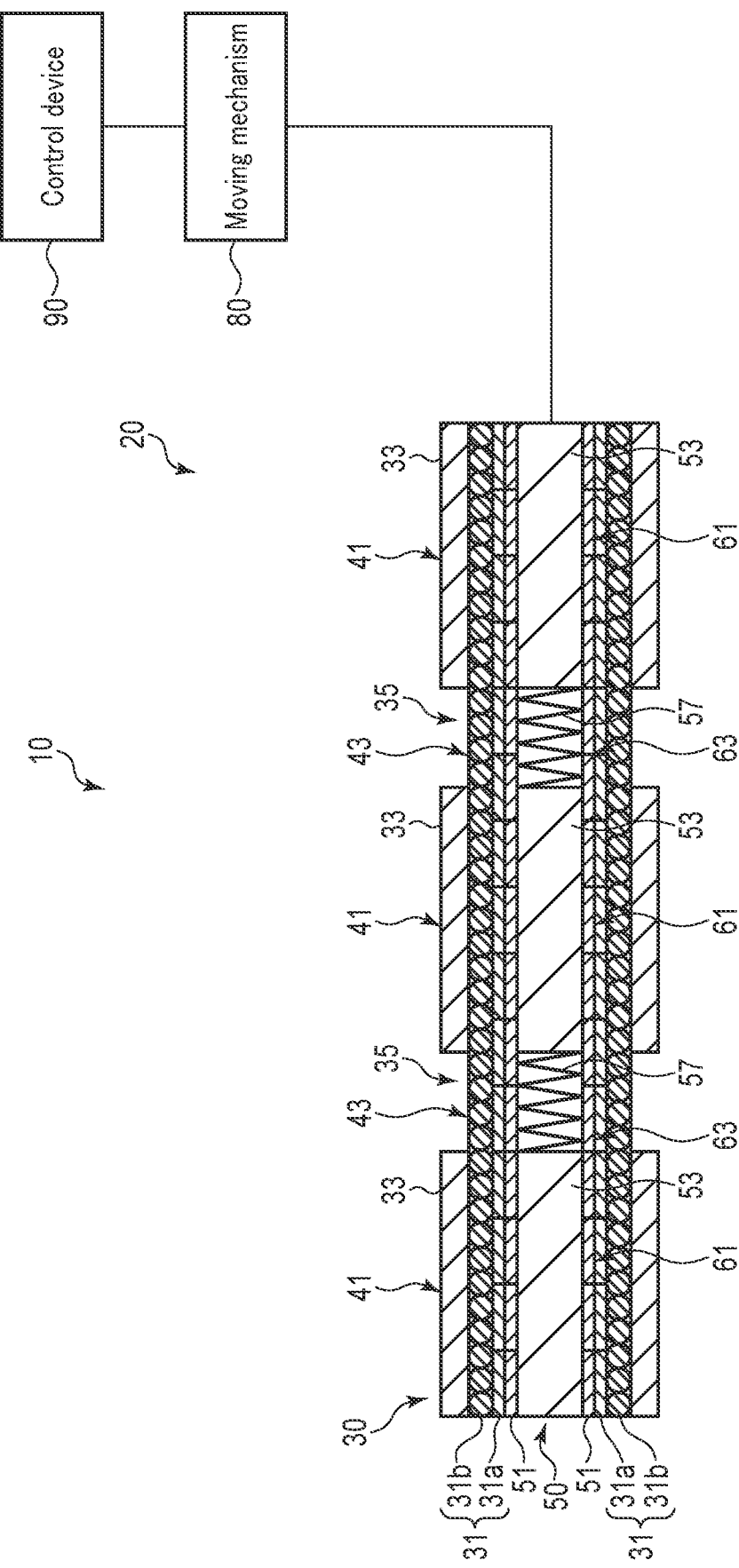
FIG. 18 is a schematic view of a variable stiffness system according to a first modification of the third embodiment.

Hereinafter, a first modification of the third embodiment will be described with reference to FIG. 18. FIG. 18 is a schematic view of a variable stiffness system according to the first modification of the third embodiment. In the present modification, only the differences from the third embodiment will be described.

In the present modification, the positions of the stranded tube 31b and the contact coil 31a are opposite to the positions thereof described in the third embodiment. That is, in the first elongated member 30 of the present modification, the first hard member 33, the stranded tube 31b, and the contact coil 31a are arranged in the mentioned order from the outside of the first elongated member 30 toward the inside of the first elongated member 30. Therefore, the contact coil 31a is arranged on the innermost layer of the first elongated member 30. The contact coil 31a guides, along the longitudinal axis direction of the first elongated member 30, the second elongated member 50 configured to move along the longitudinal axis direction of the first elongated member 30 with respect to the first elongated member 30.

The outer peripheral surface of the stranded tube 31b is fixed to the inner peripheral surface of the first hard member 33 covering the outer peripheral surface by, for example, bonding or welding.

The outer peripheral surfaces of both ends of the contact coil 31a are fixed to the inner peripheral surface of the stranded tube 31b covering both ends of the contact coil 31a by, for example, bonding or welding.

The first high bending stiffness section 41 includes the first hard member 33, a part of the stranded tube 31b, the part being arranged inside the first hard member 33, and a part of the contact coil 31a, the part being arranged inside the part of the stranded tube 31b.

The first low bending stiffness section 43 includes a part of the stranded tube 31b and a part of the contact coil 31a, the parts being not arranged inside the first hard member 33, in other words, the parts being not covered with the first hard member 33 and are exposed from the first hard member 33.

Even in such an arrangement, the present modification can achieve an effect against the compressive force and the tensile force in about the same manner as the third embodiment.

Second Modification of Third Embodiment

Figure 19:
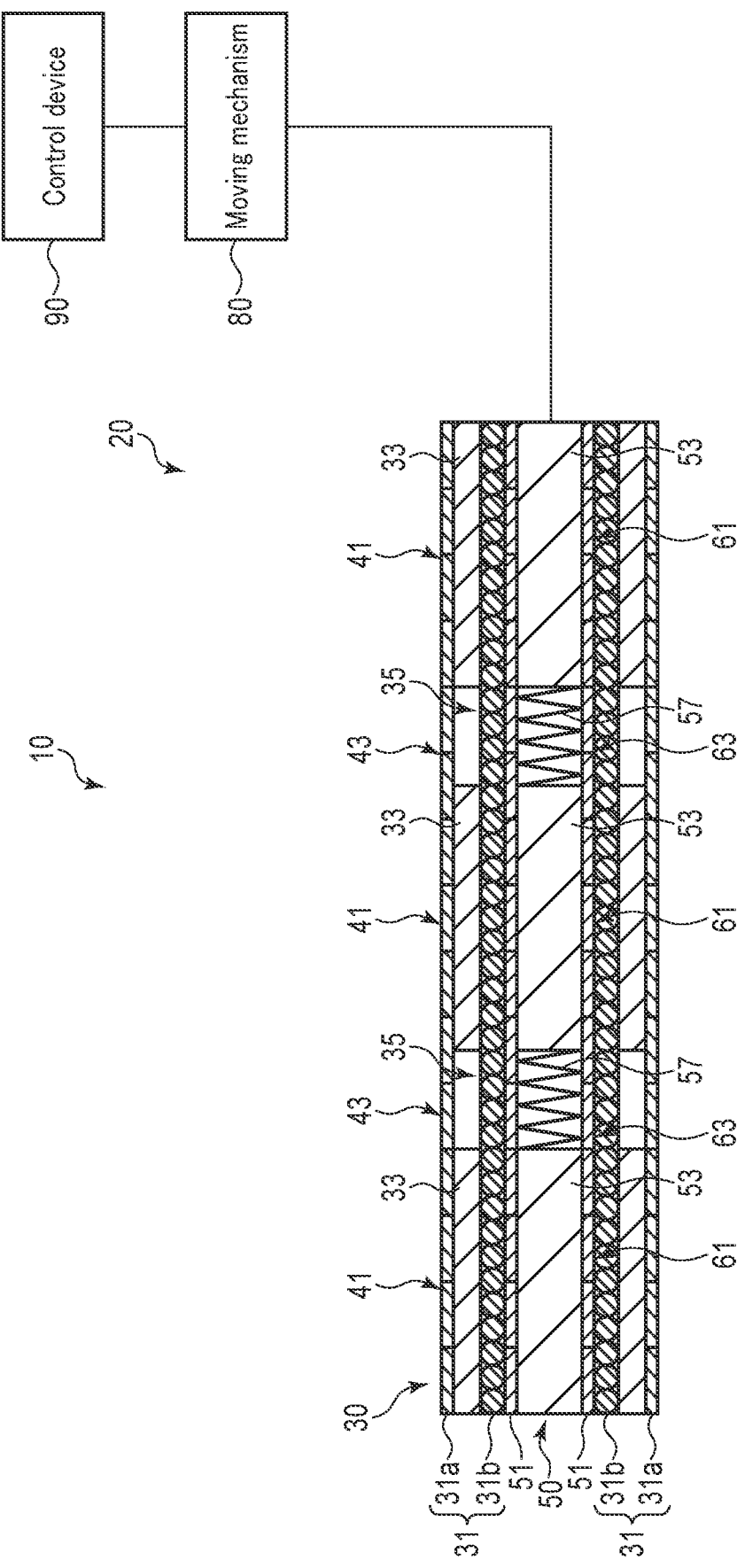
FIG. 19 is a schematic view of a variable stiffness system according to a second modification of the third embodiment.

Hereinafter, a second modification of the third embodiment will be described with reference to FIG. 19. FIG. 19 is a schematic view of a variable stiffness system according to the second modification of the third embodiment. In the present modification, only the differences from the third embodiment will be described.

In the present modification, the position of the contact coil 31a is different from the position thereof described in the third embodiment. That is, in the first elongated member 30 of the present modification, the contact coil 31a, the first hard member 33, and the stranded tube 31b are arranged in the mentioned order from the outside of the first elongated member 30 toward the inside of the first elongated member 30. Therefore, the contact coil 31a is arranged on the outermost layer of the first elongated member 30, and the stranded tube 31b is arranged on the innermost layer of the first elongated member 30. The contact coil 31a guides, along the longitudinal axis direction of the first elongated member 30, the second elongated member 50 configured to move along the longitudinal axis direction of the first elongated member 30 with respect to the first elongated member 30.

The contact coil 31a covers the first hard members 33, and the inner peripheral surface of the contact coil 31a is fixed to the outer peripheral surfaces of the first hard members 33 by, for example, bonding or welding.

The outer peripheral surfaces of both ends of the stranded tube 31b are fixed to the inner peripheral surfaces of the first hard members 33 covering both ends of the stranded tube 31b by, for example, bonding or welding.

The first high bending stiffness section 41 includes a part of the contact coil 31a, the part covering the first hard member 33, the first hard member 33, and a part of the stranded tube 31b, the part being arranged inside the first hard member 33.

The first low bending stiffness section 43 includes a part of the contact coil 31a, the part not covering the first hard member 33 and a part of the stranded tube 31b, the part being not arranged inside the first hard member 33, in other words, the part being not covered with the first hard member 33 and being exposed from the first hard member 33.

Even in such an arrangement, the present modification can achieve an effect that is about the same as that of the third embodiment.

Fourth Embodiment

Figure 20:
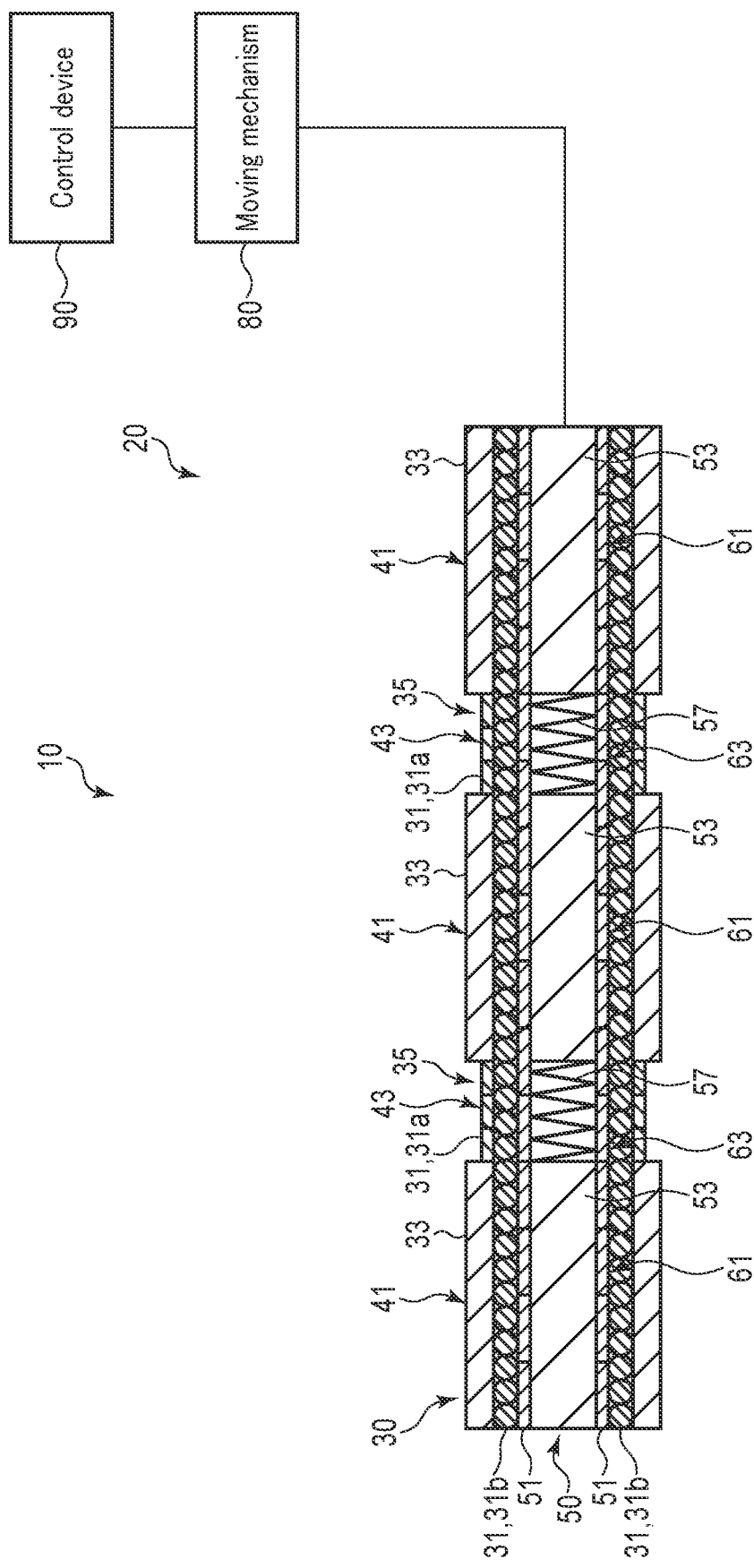
FIG. 20 is a schematic view of a variable stiffness system according to a fourth embodiment of the present invention.

Hereinafter, the fourth embodiment of the present invention will be described with reference to FIG. 20. FIG. 20 is a schematic view of a variable stiffness system according to the fourth embodiment of the present invention. In the present embodiment, only the differences from the third embodiment will be described.

In the first elongated member 30 of the present embodiment, the first hard member 33 and the contact coil 31a, which are in the same layer, and the stranded tube 31b are arranged in the mentioned order from the outside of the first elongated member 30 toward the inside of the first elongated member 30. Therefore, the stranded tube 31b is arranged on the innermost layer of the first elongated member 30. The stranded tube 31b guides, along the longitudinal axis direction of the first elongated member 30, the second elongated member 50 configured to move along the longitudinal axis direction of the first elongated member 30 with respect to the first elongated member 30.

The contact coil 31a is arranged in the first space 35. Therefore, the first hard members 33 and the contact coils 31a are alternately arranged on the outer peripheral surfaces of the contact coils 31a in the longitudinal axis direction of the first elongated member 30. The contact coils 31a arranged between the first hard members 33 are arranged for positioning the first hard members 33.

The outer peripheral surface of the stranded tube 31b is covered with the first hard members 33 and the contact coils 31a, and the stranded tube 31b is arranged inside the first hard members 33 and inside the contact coils 31a.

For example, the ends of the contact coils 31a are fixed to the ends of the first hard members 33 adjacent to the ends of the contact coils 31a by, for example, bonding or welding. The outer peripheral surfaces of both ends of the stranded tube 31b are fixed to the inner peripheral surfaces of the first hard members 33 covering both ends by, for example, bonding or welding. That is, the first hard member 33 arranged at the center among the three first hard members 33 need not be fixed to the stranded tube 31b.

The outer diameter of the spiral contact coil 31a is smaller than the outer diameter of the first hard member 33, but may be about the same as the outer diameter of the first hard member 33.

The first high bending stiffness section 41 includes the first hard member 33 and a part of the stranded tube 31b, the part being arranged inside the first hard member 33.

The first low bending stiffness section 43 includes the contact coil 31a arranged next to the first hard member 33 and a part of the stranded tube 31b, the part being arranged inside the contact coil 31a.

In the present embodiment, since the contact coils 31*a* are arranged in the same layer as the first hard members 33, the first elongated member 30 can be formed in two layers, and the first elongated member 30 and the variable stiffness device 20 can be made thin. Therefore, the flexible member 101 can also be made thin.

Since both ends of the contact coils 31*a* and both ends of the stranded tube 31*b* are fixed, the movement of the contact coils 31*a* and the stranded tube 31*b* with respect to the first hard members 33 in the longitudinal axis direction of the first elongated member 30 can be regulated.

The ends of the contact coils 31*a* may be in contact with the ends of the first hard members 33 adjacent to the ends of the contact coils 31*a* without being fixed thereto. The inner peripheral surfaces of the contact coils 31*a* may be fixed to the outer peripheral surface of the stranded tube 31*b* by, for example, bonding or welding.

Note that the invention of the present application is not limited to the above embodiments and can be variously modified in a range not departing from the gist in an implementation stage. In addition, the embodiments may be implemented in appropriate combinations as much as possible, and in that case, combined effects are obtained. Furthermore, the above embodiments include inventions at various stages, and various inventions can be extracted by appropriate combinations of plural constituent elements disclosed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness device comprising:
   a first elongated member; and
   a second elongated member movable along the first elongated member,
   the first elongated member including first high bending stiffness sections, first low bending stiffness sections having a bending stiffness lower than a bending stiffness of the first high bending stiffness sections, and a reinforcement member reinforcing a strength of the first elongated member, the reinforcement member being of a metal material and having a hollow shape,
   the reinforcement member including a contact coil formed of a first wire, the first wire being arranged substantially perpendicular to a longitudinal axis direction of the reinforcement member and spirally wound around a longitudinal axis of the reinforcement member, and a stranded tube formed of second wires, the second wires being arranged substantially in parallel to the longitudinal axis direction of the reinforcement member and twisted around each other,
   the second elongated member including at least one second high bending stiffness section, and at least one second low bending stiffness section having a bending stiffness lower than a bending stiffness of the second high bending stiffness section,
   the second elongated member being configured to move inside the reinforcement member along the longitudinal axis direction of the reinforcement member, so as to change a position of the second elongated member with respect to the first elongated member, thereby varying a stiffness of a part of the variable stiffness device.

2. The variable stiffness device according to claim 1, wherein
   both ends of the stranded tube and both ends of the contact coil are fixed.

3. The variable stiffness device according to claim 1, wherein:
   the first high bending stiffness section includes a first hard member having a tubular shape, a part of the contact coil, the part being arranged inside the first hard member, and a part of the stranded tube, the part being arranged inside the part of the contact coil; and
   the first low bending stiffness section includes a part of the contact coil, the part being exposed from the first hard member, and a part of the stranded tube.

4. The variable stiffness device according to claim 1, wherein:
   the first high bending stiffness section includes a first hard member having a tubular shape, a part of the stranded tube, the part being arranged inside the first hard member, and a part of the contact coil, the part being arranged inside the part of the stranded tube; and
   the first low bending stiffness section includes a part of the stranded tube, the part being exposed from the first hard member, and a part of the contact coil.

5. The variable stiffness device according to claim 1, wherein:
   the first high bending stiffness section further includes the contact coil, a first hard member having a tubular shape and arranged inside the contact coil, and a part of the stranded tube, the part being arranged inside the first hard member; and
   the first low bending stiffness section includes a part of the contact coil, the part not covering the first hard member, and a part of the stranded tube, the part being exposed from the first hard member.

6. The variable stiffness device according to claim 1, wherein:
   the first high bending stiffness section further includes a first hard member having a tubular shape, and a part of the stranded tube, the part being arranged inside the first hard member; and
   the first low bending stiffness section includes the contact coil arranged in a same layer as the first hard member, and a part of the stranded tube, the part being arranged inside the contact coil.

7. The variable stiffness device according to claim 1, wherein:
   the first high bending stiffness section includes a first hard member having a tubular shape, and a part of the reinforcement member, the part being arranged inside the first hard member;
   the first low bending stiffness section includes a part of the reinforcement member, the part being exposed from the first hard member; and
   the first high bending stiffness section and the first low bending stiffness section are alternately arranged in the longitudinal axis direction of the reinforcement member.

8. The variable stiffness device according to claim 7, wherein:
   the second high bending stiffness section includes a second hard member, and a part of a tubular member, the part covering the second hard member;
   the second low bending stiffness section includes a soft member softer than the second hard member, and a part of the tubular member, the part covering the soft member; and the second high bending stiffness section and the second low bending stiffness section are alternately arranged in the longitudinal axis direction of the tubular member.

9. The variable stiffness device according to claim 8, wherein the tubular member comprises a stranded tube formed of metal wires twisted around each other.

10. The variable stiffness device according to claim 8, wherein the tubular member comprises a contact coil.

11. The variable stiffness device according to claim 1, comprising a moving mechanism configured to move the second elongated member with respect to the first elongated member.

12. The variable stiffness device according to claim 11, wherein:

the variable stiffness device is installed in a flexible member and configured so that a positional state of the second elongated member with respect to the first elongated member is switched by the movement of the second elongated member, the positional state being switched between a first state in which the flexible member is provided with a first stiffness and a second state in which the flexible member is provided with a second stiffness higher than the first stiffness;

in the first state, the second low bending stiffness section is arranged on a periphery of the first low bending stiffness section, and the second high bending stiffness section is arranged on a periphery of the first high bending stiffness section; and in the second state, the second high bending stiffness section is arranged on a periphery of the first low bending stiffness section, and the second low bending stiffness section is arranged on a periphery of the first high bending stiffness section.

13. An endoscope comprising:

a flexible member; and the variable stiffness device according to claim 1 that is installed in the flexible member and configured to provide the flexible member with different levels of stiffness.

14. A stiffness varying method of a variable stiffness device, the variable stiffness device comprising:

a first elongated member; and a second elongated member movable along the first elongated member, the first elongated member including first high bending stiffness sections, first low bending stiffness sections having a bending stiffness lower than a bending stiffness of the first high bending stiffness sections, and a reinforcement member reinforcing a strength of the first elongated member, the reinforcement member being of a metal material and having a hollow shape;

the reinforcement member including a contact coil formed of a first wire, the first wire being arranged substantially perpendicular to a longitudinal axis direction of the reinforcement member and spirally wound around a longitudinal axis of the reinforcement member, and a stranded tube formed of second wires, the second wires being arranged substantially in parallel to the longitudinal axis direction of the reinforcement member and twisted around each other;

the second elongated member including at least one second high bending stiffness section, and at least one second low bending stiffness section having a bending stiffness lower than a bending stiffness of the second high bending stiffness section, the stiffness varying method comprising moving the second elongated member inside the reinforcement member along the longitudinal axis direction of the reinforcement member, so as to change a position of the second elongated member with respect to the first elongated member, thereby varying a stiffness of a part of the variable stiffness device.

\* \* \* \* \*